US008882704B2

(12) United States Patent
Fago et al.

(10) Patent No.: US 8,882,704 B2
(45) Date of Patent: Nov. 11, 2014

(54) INJECTOR

(75) Inventors: Frank M. Fago, Mason, OH (US);
Charles Neer, Cincinnati, OH (US);
Jonathon D. Gibbs, Mason, OH (US)

(73) Assignee: Mallinckrodt LLC, Hazelwood, MO (US)

( * ) Notice: Subject to any disclaimer, the term of this patent is extended or adjusted under 35 U.S.C. 154(b) by 49 days.

(21) Appl. No.: 13/080,499

(22) Filed: Apr. 5, 2011

(65) Prior Publication Data

US 2011/0184281 A1    Jul. 28, 2011

Related U.S. Application Data

(60) Continuation of application No. 12/247,601, filed on Oct. 8, 2008, which is a continuation of application No. 10/948,921, filed on Sep. 24, 2004, now abandoned, which is a division of application No. 10/211,726, filed on Aug. 2, 2002, now Pat. No. 6,929,619.

(51) Int. Cl.
*A61M 31/00*            (2006.01)
(Continued)

(52) U.S. Cl.
CPC ....... *A61M 5/14546* (2013.01); *A61M 5/16827* (2013.01); *A61M 2005/1403* (2013.01);
(Continued)

(58) Field of Classification Search
CPC .......... A61M 5/14546; A61M 5/1458; A61M 2005/14573; A61M 2005/2437; A61M 2005/244

USPC ............... 604/432, 431, 151–4, 232–5, 65–7; 128/DIG. 1, DIG. 12
See application file for complete search history.

(56) References Cited

U.S. PATENT DOCUMENTS

| | | | |
|---|---|---|---|
| 3,812,843 A | 5/1974 | Wootten et al. | |
| 3,964,139 A | 6/1976 | Kleinmann et al. | |

(Continued)

FOREIGN PATENT DOCUMENTS

| | | |
|---|---|---|
| EP | 0584531 | 3/1994 |
| EP | 0916353 | 5/1999 |

(Continued)

OTHER PUBLICATIONS

Angiomat 6000 Operator's Manual, Date: Jun. 1992.

(Continued)

*Primary Examiner* — Andrew Gilbert
(74) *Attorney, Agent, or Firm* — Russell T. Manning; Marsch Fischmann & Breyfogle LLP

(57) ABSTRACT

An injector automatic limiting of the operating pressure of the injector as determined by the selection of a flow rate; a syringe cradle having a warming capability; a purge/retract trigger for control of the injection procedure having intuitive direction (i.e., forward for injecting, reverse for filing), non-contact control transmission through the housing of an injector for an improved seal integrity, a speed lock, and/or the ability to change the concentration and/or flow rate of media or other fluid during an injection procedure; a switch to determine when the drive ram is in a "home" position; a "soft" on/off power switch separate from the injector; and a structure to prevent rotation of the drive ram about its axis of symmetry. Additionally, the injector system includes software for the control of various components.

30 Claims, 9 Drawing Sheets

(51) Int. Cl.
   *A61M 1/00*     (2006.01)
   *A61M 5/00*     (2006.01)
   *A61M 5/145*    (2006.01)
   *A61M 5/315*    (2006.01)
   *A61M 5/168*        (2006.01)
   *A61M 5/14*         (2006.01)
   *A61M 5/172*        (2006.01)
   *A61M 5/44*         (2006.01)

(52) U.S. Cl.
   CPc .............. *A61M 2005/14553* (2013.01); *A61M 2205/3561* (2013.01); *A61M 5/172* (2013.01); *A61M 2205/702* (2013.01); *A61M 5/007* (2013.01); *A61M 2005/1402* (2013.01); *A61M 5/31525* (2013.01); *A61M 5/1458* (2013.01); *A61M 2205/3331* (2013.01); *A61M 5/14566* (2013.01); *A61M 2205/3317* (2013.01); *A61M 2205/3653* (2013.01); *A61M 2205/3569* (2013.01); *A61M 5/445* (2013.01)
   USPC .......................... 604/67; 604/152; 600/432

(56) References Cited

U.S. PATENT DOCUMENTS

| | | |
|---|---|---|
| 3,983,363 A | 9/1976 | Alter |
| 4,217,993 A | 8/1980 | Jess et al. |
| 4,265,618 A | 5/1981 | Herskovitz et al. |
| 4,422,942 A | 12/1983 | Allington |
| 4,460,355 A | 7/1984 | Layman |
| 4,560,979 A | 12/1985 | Rosskopf |
| 4,628,499 A | 12/1986 | Hammett |
| 4,634,431 A | 1/1987 | Whitney et al. |
| 4,650,465 A | 3/1987 | Langer et al. |
| 4,743,228 A | 5/1988 | Butterfield |
| 4,755,172 A | 7/1988 | Baldwin |
| 4,812,724 A | 3/1989 | Langer et al. |
| 4,854,324 A | 8/1989 | Hirschman et al. |
| 4,913,703 A | 4/1990 | Pasqualucci et al. |
| 4,931,041 A | 6/1990 | Faeser |
| 4,950,246 A | 8/1990 | Muller |
| 4,994,984 A | 2/1991 | Massimo |
| 5,069,225 A | 12/1991 | Okamura |
| 5,078,698 A | 1/1992 | Stiehl et al. |
| 5,135,511 A | 8/1992 | Houghton et al. |
| 5,178,609 A | 1/1993 | Ishikawa |
| 5,242,408 A | 9/1993 | Jhuboo et al. |
| D341,760 S | 11/1993 | Armbruster et al. |
| 5,261,884 A | 11/1993 | Stern et al. |
| 5,269,762 A | 12/1993 | Armbruster et al. |
| 5,295,966 A | 3/1994 | Stern et al. |
| 5,300,031 A * | 4/1994 | Neer et al. ................ 604/154 |
| 5,322,511 A | 6/1994 | Armbruster et al. |
| 5,383,858 A | 1/1995 | Reilly et al. |
| 5,425,716 A | 6/1995 | Kawasaki et al. |
| D360,462 S | 7/1995 | Armbruster et al. |
| 5,505,704 A | 4/1996 | Pawelka et al. |
| 5,509,901 A | 4/1996 | Milijasevic |
| 5,512,730 A | 4/1996 | Spinello |
| 5,520,653 A | 5/1996 | Reilly et al. |
| D370,974 S | 6/1996 | Barresi et al. |
| 5,545,140 A * | 8/1996 | Conero et al. ............... 604/154 |
| 5,611,784 A | 3/1997 | Barresi et al. |
| 5,662,612 A * | 9/1997 | Niehoff ....................... 604/155 |
| 5,672,155 A | 9/1997 | Riley et al. |
| 5,741,232 A | 4/1998 | Reilly et al. |
| 5,779,675 A | 7/1998 | Reilly et al. |
| 5,795,333 A | 8/1998 | Reilly et al. |
| RE35,979 E | 12/1998 | Reilly et al. |
| 5,865,805 A * | 2/1999 | Ziemba ..................... 604/154 |
| 5,873,861 A | 2/1999 | Hitchins et al. |
| 5,899,885 A | 5/1999 | Reilly et al. |
| 5,925,022 A | 7/1999 | Battiato et al. |
| 5,928,197 A | 7/1999 | Niehoff |
| 5,938,637 A | 8/1999 | Austin et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Rhinehart et al. |
| 5,954,736 A | 9/1999 | Bishop et al. |
| 5,968,015 A | 10/1999 | Yamamoto |
| 5,997,502 A | 12/1999 | Reilly et al. |
| 6,017,326 A | 1/2000 | Pasqualucci et al. |
| 6,042,565 A | 3/2000 | Hirschman et al. |
| D422,356 S | 4/2000 | Marano et al. |
| 6,048,334 A | 4/2000 | Hirschman et al. |
| 6,059,754 A | 5/2000 | Pasch et al. |
| 6,080,136 A | 6/2000 | Trull et al. |
| 6,090,064 A | 7/2000 | Reilly et al. |
| 6,090,071 A | 7/2000 | Kriesel |
| 6,091,058 A | 7/2000 | Faries, Jr. et al. |
| 6,099,502 A | 8/2000 | Duchon et al. |
| 6,159,183 A | 12/2000 | Neer et al. |
| 6,200,289 B1 | 3/2001 | Hochman et al. |
| 6,221,045 B1 | 4/2001 | Duchon et al. |
| 6,241,708 B1 | 6/2001 | Reilly et al. |
| 6,245,041 B1 | 6/2001 | Kriesel |
| 6,245,043 B1 | 6/2001 | Villette |
| 6,254,572 B1 | 7/2001 | Knipfer et al. |
| 6,259,067 B1 | 7/2001 | Faries, Jr. et al. |
| 6,269,340 B1 | 7/2001 | Ford et al. |
| 6,276,567 B1 | 8/2001 | Diaz et al. |
| 6,312,410 B1 | 11/2001 | Yamamoto |
| 6,322,535 B1 | 11/2001 | Hitchins et al. |
| RE37,487 E | 12/2001 | Reilly et al. |
| 6,336,913 B1 | 1/2002 | Spohn et al. |
| 6,344,030 B1 * | 2/2002 | Duchon et al. ............. 604/131 |
| 6,368,307 B1 * | 4/2002 | Ziemba et al. ............. 604/218 |
| 6,371,938 B1 | 4/2002 | Reilly et al. |
| 6,402,717 B1 | 6/2002 | Reilly et al. |
| 6,428,509 B1 * | 8/2002 | Fielder ........................ 604/154 |
| 6,454,743 B1 | 9/2002 | Weber |
| 6,475,192 B1 | 11/2002 | Reilly et al. |
| 6,582,408 B1 | 6/2003 | Buch-Rasmussen et al. |
| 6,607,508 B2 | 8/2003 | Knauer |
| 6,610,033 B1 | 8/2003 | Melanson et al. |
| 6,652,489 B2 * | 11/2003 | Trocki et al. ................ 604/154 |
| 6,656,157 B1 | 12/2003 | Duchon et al. |
| 6,673,033 B1 | 1/2004 | Sciulli et al. |
| 6,673,048 B1 | 1/2004 | Duchon et al. |
| 6,676,634 B1 | 1/2004 | Spohn et al. |
| 6,676,635 B2 * | 1/2004 | Nemoto ....................... 604/154 |
| 6,716,195 B2 | 4/2004 | Nolan, Jr. et al. |
| 6,743,205 B2 | 6/2004 | Nolan, Jr. et al. |
| 6,808,513 B2 | 10/2004 | Reilly et al. |
| 6,854,620 B2 | 2/2005 | Ramey |
| 6,929,619 B2 | 8/2005 | Fago et al. |
| 6,958,053 B1 | 10/2005 | Reilly |
| 6,974,443 B2 | 12/2005 | Reilly et al. |
| 7,018,361 B2 | 3/2006 | Gillespie, Jr. et al. |
| 7,025,757 B2 | 4/2006 | Reilly et al. |
| 7,029,459 B2 | 4/2006 | Reilly |
| 7,081,105 B2 | 7/2006 | Reilly et al. |
| 7,150,724 B2 * | 12/2006 | Morris et al. .............. 604/131 |
| 7,632,246 B2 | 12/2009 | Fago et al. |
| 7,691,085 B2 * | 4/2010 | Dedig et al. ............... 604/151 |
| 7,854,726 B2 | 12/2010 | Fago et al. |
| 2001/0021823 A1 | 9/2001 | Nemoto |
| 2001/0047153 A1 | 11/2001 | Trocki et al. |
| 2002/0107481 A1 | 8/2002 | Reilly et al. |
| 2002/0165491 A1 | 11/2002 | Reilly |
| 2002/0183616 A1 * | 12/2002 | Toews et al. .............. 600/432 |
| 2003/0018252 A1 | 1/2003 | Duchon et al. |
| 2003/0028145 A1 | 2/2003 | Duchon et al. |
| 2003/0120212 A1 * | 6/2003 | Dedig et al. .............. 604/151 |
| 2003/0233069 A1 | 12/2003 | Gillespie, Jr. et al. |
| 2004/0015124 A1 | 1/2004 | Sciulli et al. |
| 2004/0068223 A1 | 4/2004 | Reilly |
| 2004/0092878 A1 | 5/2004 | Flaherty |
| 2005/0059932 A1 | 3/2005 | Reilly et al. |

(56) References Cited

U.S. PATENT DOCUMENTS

| | | |
|---|---|---|
| 2005/0187572 A1 | 8/2005 | Johnston et al. |
| 2007/0156083 A1 | 7/2007 | Johnston et al. |

FOREIGN PATENT DOCUMENTS

| | | |
|---|---|---|
| EP | 0919251 | 6/1999 |
| GB | 1168263 | 10/1969 |
| JP | 02166516 | 6/1990 |
| JP | 03102020 | 4/1991 |
| JP | 5-42338 | 8/1993 |
| JP | 09154944 | 6/1997 |
| JP | 11155949 | 6/1999 |
| JP | 2002-11096 | 1/2000 |
| WO | 96-32887 | 10/1996 |
| WO | 9736635 | 10/1997 |
| WO | 98-22168 | 5/1998 |
| WO | 0108730 | 2/2001 |
| WO | 02-04049 | 1/2002 |
| WO | 0207812 | 1/2002 |
| WO | WO02/056947 A1 * | 7/2002 |

OTHER PUBLICATIONS

Angiomat 6000 Digital Injection System Parts Manual, Date Dec. 1991.

Angiomat 6000 Digital Injection System Installation and Service Manual, Date: Dec. 1991.

* cited by examiner

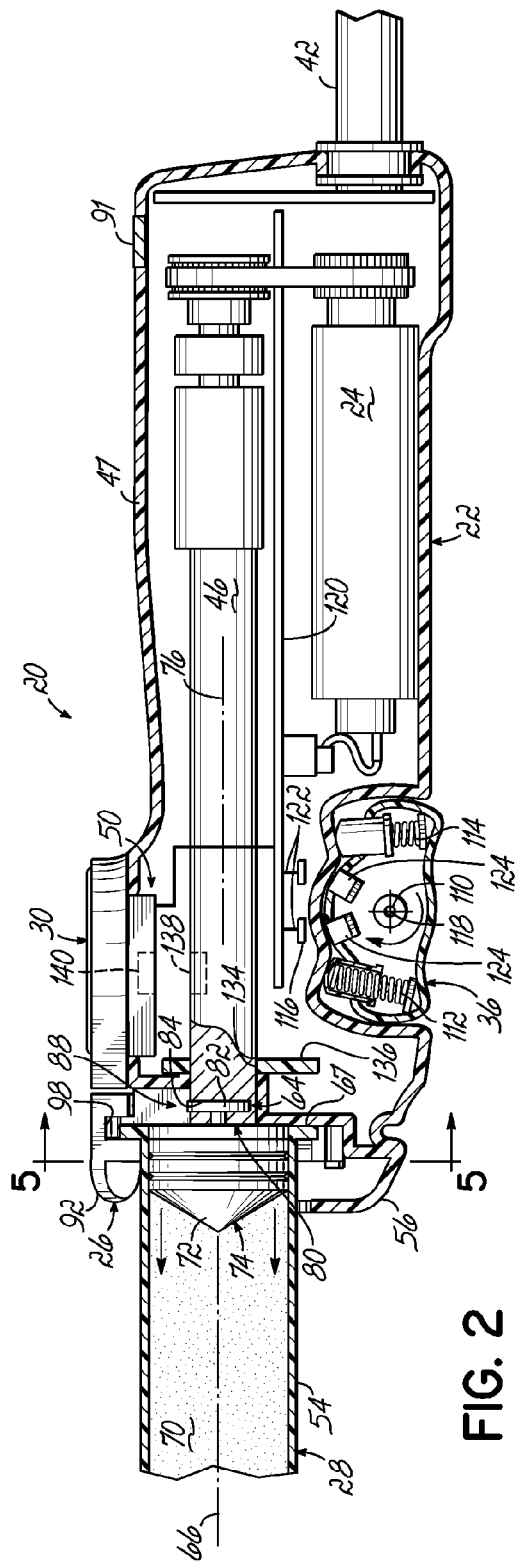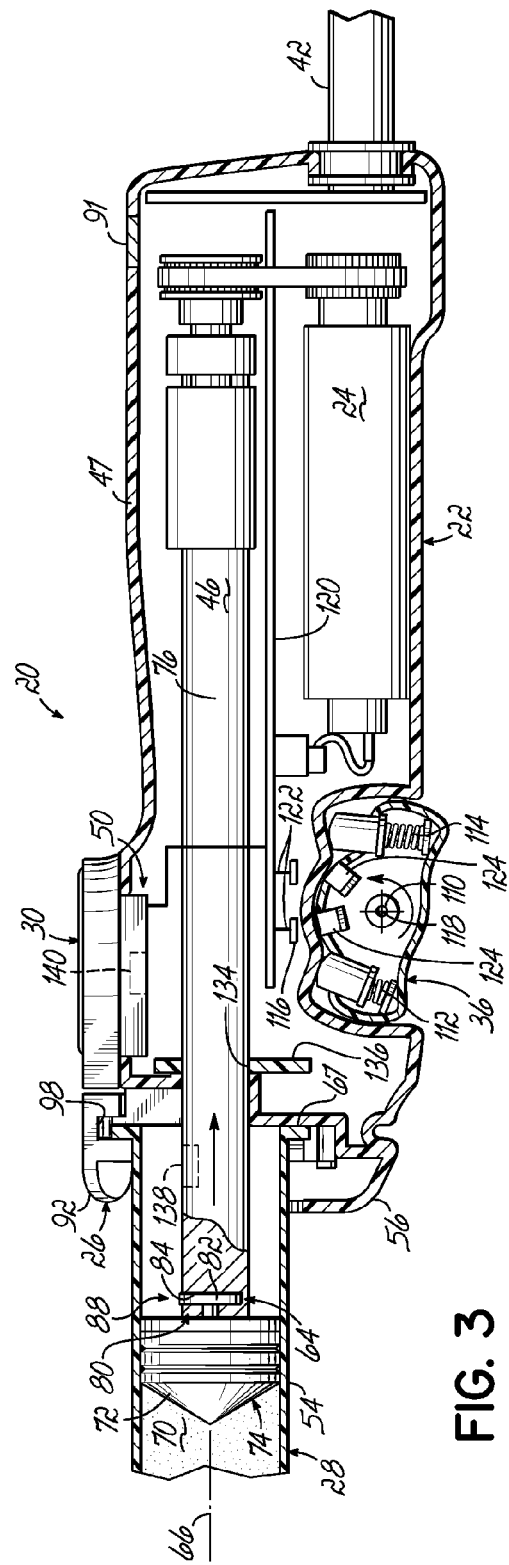

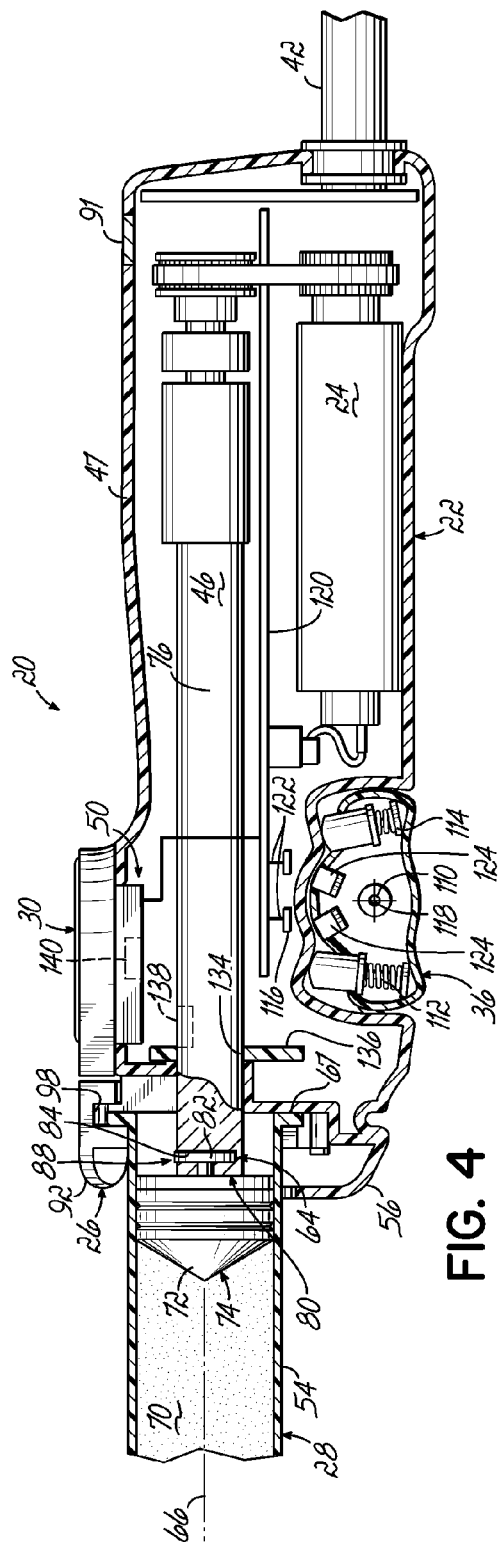

INJECTOR

CROSS-REFERENCE TO RELATED APPLICATIONS

This application is a continuation of U.S. patent application Ser. No. 12/247,601, entitled "Injector," and filed on Oct. 8, 2008, which is a continuation of U.S. patent application Ser. No. 10/948,921, entitled "Injector," and filed on Sep. 24, 2004 (now abandoned), which is a divisional of U.S. patent application Ser. No. 10/211,726, entitled "Injector," and filed on Aug. 2, 2002 (now U.S. Pat. No. 6,929,619). Priority is claimed to each of the above-noted patent applications, and the entire disclosure of each such patent application is hereby incorporated by reference.

FIELD OF INVENTION

The present invention relates to injectors for injecting fluid into animal subjects, including humans.

BACKGROUND

During many medical procedures, various fluids are injected into patients for purposes of diagnosis or treatment. An example of one such fluid is contrast media used to enhance angiography or CT imaging. Such fluids may also be used in other modalities, such as intravenous pyelogram (IVP) and cardiology. The injectors used in these procedures are often automated devices that expel the fluid from a syringe, through a tube, and into the subject.

Injectors suitable for these applications generally include relatively large volume syringes and are capable of producing relatively large flow rates and injection pressures. For these reasons, injectors for such applications typically include large, high mass injection motors and drive trains. These are typically housed in an injection head, which is supported by a floor, wall, or ceiling mounted arm. Certain such injectors include the CT9000 ADV and the Optistar MR Injection System (K948088). Such devices are generally designed to meet both the ordinary needs of the market as well as advanced needs.

There exist many drawbacks to the large injector units described above, which are presently used to inject contrast media and other media. For example, these large power injectors generally are only available at a high cost. In many instances, this cost is prohibitive in that it prices many of these injectors out of the range of some small hospitals, and out of the range of developing and third world markets. This results in patients that either (1) do without tests and treatments which may be necessary, or (2) endure the burden of travel, often over long distances, to reach those facilities with the necessary injection capabilities. Also, this results in injection procedures wherein the contrast media, or other fluid, is delivered by a hand syringe, which is ergonomically unsafe and can lead to cumulative stress disorders for the user. Further, the use of a hand syringe provides inferior images as compared to those generated when using a power injector. Additionally, many costly, large injector units may include a number of features which may not be necessary for the purposes for which they are to be used at some smaller hospitals and other medical facilities. Such facilities may be better served by an injector which does not include all the numerous features of large injectors, but which might thereby be more affordable.

In addition to the cost concerns discussed above, safety concerns can arise due to the use of these large, and often complex, injectors. First, these injectors operate at relatively high pressures, as described above. Many current power injectors have a maximum pressure limit in order to provide safety to the components of the power injector. This prevents the injector from being damaged by being subjected to forces greater than its components are rated to withstand. These injectors also allow the operator to reduce the set maximum pressure limit to provide safety to a patient or other subject to be injected. For example, access ports are inserted into patients who need medication intravenously, but whose veins cannot tolerate multiple needle sticks. Access ports that are implanted into patients cannot tolerate many of the high pressures capable of being generated by these large injectors. High flow rates and pressures can cause the implanted catheter portion of the access port to break and require surgery to remove. For example, 100 psi is generally a threshold of pressure that a typical access port is able to withstand. However, a typical large CT injector can attain pressures during delivery of media of 300 psi at all flow rates. Thus, unless the pressure of such an injector is manually reduced, the access ports in a patient can be become over-pressured and possibly fail. Limiting the pressure for the injection of fluid into an access port for a contrast study requires a technologist to reprogram the injector to reduce the pressure limit. If the technologist forgets to reset the limit to the higher setting once the application has been performed, the desired flow rates may not be achieved during injections for subsequent patients. This can result in ineffective injections and a waste of media, among other costs attendant to repeating the injection procedure.

A second safety concern regards the structure and function of the triggers of injectors. Injectors, as described above, may include a trigger lever which may be manipulated by an operator in order to dispel media or other fluid from a syringe into a subject or to pull fluid from a container and into a syringe. The triggers of these large power injectors may often operate only at a constant set speed. Once the injection has begun, it may automatically proceed to completion at a set pressure and flow rate. An operator may be generally unable to change the injection speed or rate or pressure as an injection is occurring, without actually halting the injection procedure. This lack of control over the pressure and flow rates at which an injection proceeds may raise safety issues for the patient or other subject being injected, should an incorrect pressure limit or flow rate be programmed. Likewise, halting an injection procedure can result in ineffective injections and waste of media, among other costs.

Additional problems arise when attaching a syringe to an injector. Many current injectors include a face plate, which is disposed at the forward end of the injector. To replace the syringe, the front face plate, which facilitates coupling between the syringe plunger and the plunger drive ram, is moved, the used syringe detached, and a fresh syringe attached. The syringes may be pre-filled or may be initially empty, to be filled after being attached to the injector. The plunger drive ram of the injector is disposed within the injector housing on one side of the face plate, while the syringe is attached to, and extends from, the opposite side of the face plate. When the syringe is connected to the face plate, it is substantially co-axially aligned with the plunger drive ram. The face plates used in operatively connecting the syringe to the injector may be cumbersome and time-consuming to operate.

Additionally, many injectors may include a separate console for controlling the injector. The console typically includes programmable circuitry which can be used for automatic programmed control of the injector. This may be beneficial in that the operation of the injector can be made predictable and operate in concert with the operations of other medical equipment. Thus, at least a part of the injection process may be automatically controlled. However, any filling procedure, and typically some part of the injection procedure may be performed by an operator using hand-operated movement controls on the injector head. Typically the hand-operated movement controls may include buttons for reverse and forward movement of the injector drive ram, to respectively fill and empty the syringe. In some cases, a combination of buttons is used to initiate movement of the ram or to control ram movement speed. The injector head also typically includes a gauge or display for indicating injection parameters to the operator. Unfortunately, operators have found it cumbersome to use the hand-operated movement buttons and to read the injector head gauges and displays.

Another problem that arises concerns the temperature of the media or other fluid as it is injected. It is often important, during injection procedures, that the fluid to be injected have a temperature approaching the body temperature of the subject to be injected. To accomplish this, in large injectors as described above, a warming unit may be included in the injector to raise and maintain the temperature of a fluid to a predetermined level. Often, media will be maintained at a particular temperature in a separate warming unit and subsequently attached to the injecting unit. However, any lag time involved in removing the media from its warming cradle, and attaching the syringe, and injecting the media, may result in a decrease of the temperature of the media.

Another drawback with presently used injectors is that they are generally incapable of communicating with other injectors. As a result this only allows for one injector to be programmed and/or used at a time. Thus, there is generally no ability for different injectors to operate automatically in a sequential fashion. This situation reduces the overall safety in injection procedures by requiring a technician or other medical personnel to operate and monitor potentially several different injections simultaneously or in overlapping fashion. This increases the potential for error in an injection procedure.

Additional problems with current injectors arise due to the use of multiple components which must communicate with one another during an injection procedure. Often, several components, such as the injector, a console, and a power supply, must all communicate with one another in order to correctly perform an injection.

Another problem that arises from the structure of current injectors is in attempting to maintain the correct placement of the drive ram in order to facilitate the loading and unloading of syringes to the injector. Many prior art injectors use potentiometers and/or encoders on the motor, either separately or as redundant systems, to track the location of the drive ram in relation to the housing of the injector. It is important to be able to track the position of the drive ram so that an operator can remove and replace syringes during a series of injections, while being able to rely on the drive ram being in the correct location. Some previous injectors have used linear potentiometers; others have used rotary potentiometers. However, the use of these potentiometers and redundant systems increases the required size and cost of the injectors.

Another problem found in current injectors is in the structure for ensuring that the drive ram does not rotate about its axis of symmetry during injection. If the drive ram should rotate away from its original position, it is possible that an operator would then be unable to remove and discard old syringes, and/or attach new syringes to the injector. To reduce this problem, previous injectors generally have used a cam follower operatively connected to the drive ram which moves back and forth along with the drive ram and tracks in a groove located in an inner wall of the housing of the injector in order to prevent rotation of the drive ram. However, this structure increases friction which may result in an unsmooth movement of the injector drive ram. Additionally, any groove in the housing may become blocked which also may disrupt the injection procedure.

SUMMARY

Accordingly, to improve power injectors, there is need for an injector system including an injector in which pressure limits may be easily set within safety thresholds. It would be further desirable to provide an injector which allows for manipulation of injection speeds, rates, and/or pressures during the injection procedure. Further, it would be desirable to provide an injector which reduces or eliminates power connections to the injector itself. It would also be desirable to provide an injector to facilitate attachment of a syringe. Further, it would be desirable to provide an injector which has the capability of warming and/or maintaining the temperature of the media or other fluid to be injected. Additionally, it would be desirable to provide an injector which is capable of communicating with other injectors. Further, it would be desirable to provide an injector which is capable of tracking the location of the drive ram while reducing the overall size, and thus the cost, of the injector. Also, it would be desirable to provide an injector which includes a uniform or "soft" power switch associated with a peripheral component, such as a remote console. Further, it would be desirable to provide an injector which prevents rotation of the drive ram. Also, it would be desirable to provide an injector which improves the ease of its operation. And finally, it would be desirable to provide such an injector at low cost in order to provide such injectors to currently unavailable markets.

The present invention also provides less cumbersome features than those injectors of the prior art, and thereby may provide injectors and injector systems at lower cost. Accordingly, the apparatus of the present invention includes an injector system having an injector which overcomes and eliminates the drawbacks of injector systems and injectors as described above in the background of the invention. The term "injector system", as used herein, generally applies to any number of injectors, consoles, power supplies, interconnections, and other peripherals used to complete an injection procedure, while the term "injector" generally refers to the particular equipment which directly discharges fluid, such as media, from a syringe. However, the terms "injector" and "injector system" may be used interchangeably herein.

The injector of the present invention may be used to deliver radiographic contrast media and/or flushing solution into a patient's vascular system for the purpose of obtaining enhanced diagnostic x-ray images. However, the injector is not limited to this purpose, and may be used to deliver other media for other applications. In one aspect, the invention provides an ergonomic, light-weight powerhead injector that may be hand-held. This allows the injector to be more portable and economical than current large mounted injectors. Such a handheld injector is amenable for use in facilities which rely upon hand injection, or for use in combination with a mounted single powerhead to provide a dual syringe capability in CT applications. The injector of the present invention may deliver radiographic contrast media at a controlled flow rate and volume into a patient's vascular system for the purpose of obtaining enhanced diagnostic images. The injector of the present invention is made up generally of at least the following components:

(1) A powerhead—The powerhead includes a drive system, a syringe mount for attachment and holding of a syringe, a main microprocessor, control electronics, a control keypad for programming and initiating injection protocols, a status display, and a purge/retract trigger.

(2) A power pack—The power pack includes a power supply and an interface. The interface is made up of a plurality of relays and optical couplings that provide communication between various devices. One use for the interface is to harmonize two injectors in one injection system so as to provide greater volume capability or to provide a flushing solution.

The present invention may also include an optional remote console which communicates with the powerhead to program and initiate injection protocols, displays the injection status, and displays a timer.

The present invention may thus include, but is not limited to, the following features: (1) a syringe mount for attachment of a syringe to the injector; (2) display and controls for volume and flow rates; (3) automatic limiting of the operating pressure of the injector as determined by the selection of a flow rate; (4) a syringe cradle having a warming capability; (5) a purge/retract trigger including a trigger lever for control of the injection procedure having intuitive direction (i.e., forward for injecting, reverse for filing) coupled with variable velocity of the drive ram, non-contact control transmission through the housing of an injector for an improved seal integrity, a speed lock, and/or the ability to change the concentration and/or flow rate of media or other fluid during an injection procedure; (6) a switch to determine when the drive ram is in a "home" position; (7) a "soft" on/off power switch separate from the injector; and (8) a structure to prevent rotation of the drive ram about its axis of symmetry. Additionally, the injector system may include software for the control of various components. It will be apparent to those of skill in the art that many of the features of the injector of the present invention may also be applicable to the large ceiling, floor, or wall mounted injectors described above in the background of the invention.

The injector of the present invention delivers media, such as contrast media for example, under pressure, into a patient for the purpose of obtaining contrast enhanced diagnostic images. As described above in the background of the invention, many current markets are served by larger, more permanent injector systems which are mounted to the exam table suspended from the ceiling, or fitted to a pedestal-type mobile stand, as described above in the background of the invention. These previous injectors may only be available at a cost that is prohibitive in many markets. In one aspect, the injector of the present invention may be small and light weight, thus allowing the user the option of holding the injector by hand during injections, thus allowing for a greater level of control. Such a small handheld injector requires less materials and may therefore be produced at a lower cost. This reduction in the overall price of such an injector increases the ability of smaller hospitals and third world markets to purchase such injectors, and thus allows patients in those areas access to a greater range of medical procedures. The injector of the present invention is designed to meet ordinary needs of the medical market and is therefore less expensive, smaller, and less complicated to operate. Features such as stored protocols, multi-phasic injections, high flow rate, and optional printer may be omitted from the injector of the present invention in order to reduce costs and simplify the user interface. With an optional injector-to-injector interface, the injector of the present invention may be joined with other compatible injectors in order to deliver multi-phasic injections, greater volume capability, or a flushing solution (normally saline) in a similar manner as some other injection systems, such as the Optistar MR injection system.

A greater level of control is also provided by the purge/retract trigger of the present invention, which includes an intuitive trigger lever. This trigger lever may be in the form of a variable speed rocker switch. Pushing on the front of the trigger of the injector of the present invention will extend the drive ram into the syringe thereby discharging any fluid contained therein. Pushing the back of the trigger will retract the ram from the syringe. The trigger of the injector of the present invention allows the operator to vary the speeds at which fluids are being injected. It does so by providing a proportional speed control for the drive ram motions of extension and retraction. The speed of the drive ram is dependent on the amount of trigger activation compared to the program speed. Thus, the further an operator displaces the trigger from its original, or home, position when pushing on the front of the lever, the faster the movement of the drive ram and thus the injection flow rate. The same speed control may be provided when retracting the drive ram.

Another aspect of the injector of the present invention is the use of noncontact control associated with the trigger in order to reduce power connections through the housing in order to seal the housing. In one embodiment, such non-contact control may occur through a series of magnets associated with the trigger, the magnets being sensed by a magnetic sensor that is operatively connected to a circuit board within the housing of the injector. Additionally, the injector of the present invention may include a speed lock associated with the trigger. This allows an operator to operate injection and filling functions of the injector at constant speeds by engaging the speed lock, or alternatively at variable speeds by disengaging the speed lock.

Another aspect of the injector of the present invention is the integrity of the connection between the injector and the syringe to be loaded into the injector. To that end, the injector of the present invention provides a syringe mount including first and second gripping members that are designed to be substantially circumferential around the cylindrical body of a syringe when the syringe is loaded into the injector. These gripping members are biased towards the longitudinal axis of the syringe so that as a syringe is placed into the injector, the gripping members bias toward and clamp around the cylindrical body of the syringe.

In another aspect, the handheld injector of the present invention may include a warming cradle that is operatively connected to the injector. This warming cradle allows the contents of a syringe to be maintained at a particular desired temperature while the syringe is attached to the injector. In one embodiment, the warming unit may be a cradle present on a hanger which can be associated with the injector of the present invention. In use, the injector (including syringe) is operatively connected to the hanger with the syringe oriented in a downward fashion. This brings the cylindrical body of the syringe into proximity with the cradle such that the media within the syringe is warmed. This configuration reduces and eliminates any cooling problems present with the use of previous separate warming units and injectors.

As described above, the present invention also allows for limitation of the pressure supplied by the injector. Since low flow rates require less pressure, the injector of the present invention automatically assigns the pressure limit based on the flow rate. The pressure limit value is thus high enough to achieve the programmed flow rate under normal conditions, but won't allow high pressure to develop in the event of unexpected restriction or blockage within the syringe or tube or access port. By automatically assigning a pressure limit based on the flow rate, an operator does not need to remember to alter the pressure limit each time the injector is used. Thus, the injector is able to deliver media at desired rate, but does not allow too much reserved pressure to build in the event that a blockage occurs. This increases the safety of the injector of the present invention over that of injectors of the prior art.

The injector of the present invention may also be adapted to be used with other injectors. These other injectors may include, but are not limited to, handheld injectors, ergonomic lightweight powerhead injectors, or other CT injectors, and may utilize multiple device communication links. In one particular embodiment of the present invention the communication format used is a Controller Area Network (CAN). However, the injector could potentially use any communication format. The communication may occur through wires, fiber optic cable, or may occur through wireless communication.

The injector of the present invention also includes a ram home detector. The ram home detector accurately detects both when the ram is a certain distance from the home position and when the ram is at the home position. This detection may be achieved through the use of magnets. This allows the elimination of secondary analog position devices such as a potentiometer. As described above in the background of the invention many present injectors use potentiometers and/or encoders on the motor as redundant systems to track the location of the drive ram of an injector. The injector of the present invention does not include such a system. Rather, the injector of the present invention includes a magnet disposed on the ram that interacts with sensors along the inner part of the injector to detect the location of the ram. When reversing the ram to its home position, for example, this allows the ram to run quickly in reverse mode until it is a certain distance from its home position. During its operation, the injector of the present invention calibrates a value which it assigns to the ram when the ram is in its home position, generally flush with the outer edge of the front surface of the injector. In this way, the ram can be run and reversed such that it always comes to a rest in the same home position. This is necessary in being able to remove and replace various syringes, into and out of the drive ram when in the correct location. Thus, when in reverse mode, the injector may reverse the ram at a relatively rapid rate until it recognizes that it is close to the home position. The rate of reversal of the ram is then slowed until the injector recognizes that it has reached the pre-calibrated home position. Movement of the ram is then halted such that syringes may be removed from and/or inserted into the injector.

Additionally, the injector of the present invention also includes an on/off power switch, referred to as a "soft" power switch, located on the remote console which is present in addition to the switch located on the power supply and/or on the injector itself. Consoles used in injection procedures generally have an off switch for DC power while the AC power of the power supply remains active. The on/off switch of the injector of the present invention communicates with the console such that if the console is in its off position, the injector and console will automatically be turned on when the power supply reads that the console has been turned on. In particular, this switch includes a normally closed/normally open contact that communicates with a processor inside the console of the injector. When the contact is open, the processor communicates with a communication component within the injector to cause the power supply to turn off. Software may be included in the injector of the present invention to ensure that the switch does not start the actual running of an injection procedure.

The injector of the present invention also includes a structure to prevent rotation of the drive ram. In particular, this prevents the ram from rotating about its axis of symmetry during an injection procedure. The anti-rotation of the ram is caused by the shape of the drive ram itself. In one embodiment, a cross-section of the drive ram taken perpendicular to the longitudinal axis of the drive ram is in the shape of back to back D's, having a flat surface across the top of the ram, a flat surface across the bottom of the ram and a curved surface on both sides of the ram. This drive ram inserts through a similarly shaped orifice 134 in a plate in the end of the housing of the injector of the present invention nearest the syringe. Due to the flat surfaces on the top and the bottom of the drive ram, the ram is thus unable to rotate as it moves forward. This is important in keeping a coupling element that is disposed at the end of the drive ram aligned in an upward facing direction so that syringes may be removed and replaced into the injector.

The aforementioned and other principles and advantages of the present invention may explained and/or be apparent from the accompanying drawings which are incorporated in and constitute a part of this specification, along with the general description of the invention given above and the detailed description of the embodiments given below.

BRIEF DESCRIPTION OF THE FIGURES

FIG. 2 is a cross-sectional view of the injector of the present invention taken along lines 2-2 of FIG. 1, and depicting the intuitive trigger of the present invention;

FIG. 3 is a cross-sectional view of the intuitive trigger of the present invention depicting the trigger in a forward position;

FIG. 4 is a cross-sectional view of the intuitive trigger of the present invention depicting the trigger in a reverse position;

FIG. 5 is a cross-sectional view of the syringe mount taken along line 5-5 of FIG. 2 depicted without a syringe attached to the injector;

FIG. 6 is a cross-sectional view of the syringe mount depicting a syringe attached to the injector of the present invention;

DETAILED DESCRIPTION

Figure 1:
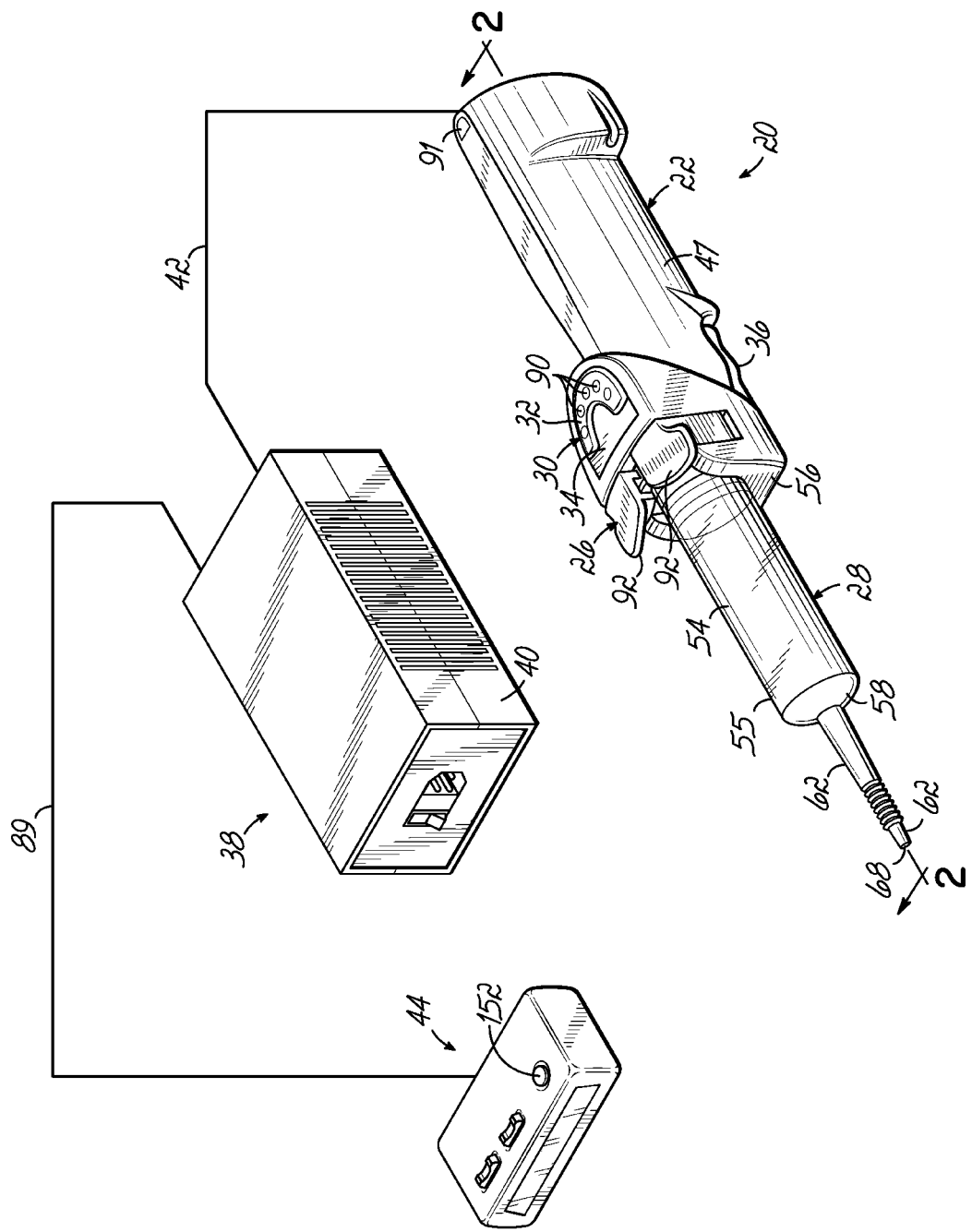
FIG. 1 is a perspective view of the injector of the present invention, depicting the intuitive trigger and the syringe mount in accordance with principles of the present invention and also including a power supply and a remote console.

As described above in the summary of the invention, the present invention provides an injector which overcomes and eliminates the drawbacks of injectors as described above. With reference to the Figures, an injector 20 of the illustrated embodiment of the present invention may be provided in a "wand" shape in order to be hand held. The injector 20 of the present invention is designed to meet ordinary needs of the medical market and is therefore less expensive, smaller, and less complicated to operate. Features such as stored protocols, multi-phasic injections, high flow rate, and optional printer may be omitted in order to reduce costs and simplify the user-injector interface 30. With an optional injector-injector interface 31 (FIG. 1A), the injector 20 of the present invention may be joined with other compatible injectors in order to deliver greater volume injections, or a flushing solution (normally saline) in a similar manner as some other injection systems such as the Optistar MR injection system. It will, however, be recognized by those of skill in the art that many of the features of the present invention are amenable for use on larger injectors, such as wall, ceiling, or floor mounted CT injectors. The injector 20 of the present invention may deliver radiographic contrast media at a controlled flow rate and volume into a patient's vascular system for the purpose of obtaining enhanced diagnostic images. As described above, the injector 20 of the present invention is made up generally of at least the following components:

(1) A powerhead 22—The powerhead 22 includes a drive system 24 which may be electromechanical, a syringe mount 26 for the attachment and holding of a syringe 28, a main microprocessor, control electronics, a user-injector interface 30 including a control keypad 32 for programming and initiating injection protocols, a status display 34, and a purge/retract trigger 36.

(2) A power pack 38—The power pack 38 includes a power supply 40 and a power-injector interface 42. In general, the power pack 38 may supply DC power to the powerhead 22 from AC mains. The power-injector interface 42 is made up of a plurality of relays and optical couplings that provide communication between devices such as the powerhead 22 and power pack 38. One use for these interfaces such as the injector-injector interface 31 is to harmonize two injectors in an injection system so as to provide greater volume capability or to provide a flushing solution.

The present invention may also include an optional remote console 44 which communicates with the powerhead 22 to allow a user to program and initiate injection protocols and control injections, such as by starting and stopping an injection. The remote console 44 also may include a user-console interface 45 which may display injection parameters such as volume and flow rate while injecting, may display the injection status, and may display a timer.

Certain features of the injector 20 of the present invention may include, but are not limited to, the following. The injector 20 of the present invention may include a syringe mount 26 on the injector 20 in order to facilitate attachment of a syringe 28 to the injector 20 in alignment with a drive ram 46. The injector 20 may include a cradle 48 having a warming capability. Further, the injector 20 of the present invention may include a purge/retract trigger 36 having intuitive direction capabilities. These include pushing the trigger 36 in a forward direction for injecting, and pushing the trigger 36 in a reverse direction for filling. Additionally, the velocity of the drive ram 46 may be varied, depending on the degree of deflection of the trigger 36 away from a "home" position. The trigger 36 also may include a non-contact control transmission through a housing 47 of the injector. The trigger 36 also may include a speed lock which allows a user to have the ability to change the concentration or flow rates of the fluid being injected during the actual operation of an injection procedure. The utility of an injector 20 that may be small and light weight along with the ability to dynamically adjust the flow rate while performing an injection gives the user greater levels of control over the injection. Further, the pressure generated by the injector 20 of the present invention may be automatically limited by the selection of a particular flow rate. The injector 20 of the present invention also may include a ram home detector 50 that is used to determine when the drive ram 46 of the injector 20 is located in a "home" position. The injector 20 of the present invention also may include an on/off power switch 52 on the remote console 44 which is separate from other power switches. Finally, the injector 20 of the present invention may also include the drive ram 46 having a particular structure that operates to prevent rotation of the drive ram 46 about its axis of symmetry 76.

As mentioned previously, the injector 20 of the present invention operates in combination with a syringe 28. Proximal to the forward end 56 of the injector housing 47, positioned between the injector 20 and the syringe 28, is a syringe mount 26 to facilitate attachment of the syringe 28 to the injector 20. In certain embodiments (not shown), a pressure jacket, preferably transparent, may extend outwardly from the forward end 56 of the housing 47, in order to receive a replaceable syringe 28. The syringe 28 and pressure jacket are constructed such that they withstand the injection pressures created by the injector 20 during an injection operation. It is not necessary that the injector 20 include a pressure jacket that surrounds the syringe 28. In an alternate embodiment (not shown), a cradle may extend outwardly from the forward end 56 of the housing 47, in order to support the syringe 28. As will be discussed below, such a cradle may have a heating capability, in order to warm the contents of the syringe 28. However, it is not necessary that the injector 20 include a cradle to support the syringe 28. In yet another embodiment, the syringe 28 may simply extend freely from the injector 20, with no structure for its support other than its connection to the injector 20 itself. The syringe 28 may include a syringe plunger.

With reference to FIGS. 1-4, the syringe 28 for use with the injector 20 of the present invention generally includes a body 54 which may be in the form of an exterior cylindrical barrel, which at its forward end 55 is integral with a conical front wall section 58. A neck 60, terminating in a discharge tip 62, generally extends forwardly from and may be integral with the conical front wall section 58. The body 54 of the syringe 28 may engage the interior wall of a pressure jacket or a cradle, as described above, when such a pressure jacket or cradle is present on the injector 20. However, the illustrated embodiment depicts a syringe 28 extending freely from the front of the injector 20. The syringe 28, as used in conjunction with the injector 20 of the present invention, includes a syringe mating section 64, which may be in the form of a radially outwardly extending flange. This syringe mating section 64 is positioned in a plane perpendicular to the axis of symmetry 66 of the syringe 28 and integral with the rear end 67 of the cylindrical barrel of the body 54 of the syringe 28. This flange may be annular. The syringe mating section 64 is arranged, when the syringe 28 is located in conjunction with the injector 20, to align proximal to cooperating members of a syringe mount 26 located on the forward end 56 of the injector housing 47. In this manner, the syringe mating section 64 and syringe mount 26 facilitate the connection of the syringe 28 to the injector 20, as will be discussed in greater detail below.

The discharge tip 62 of the syringe 28 generally contains an orifice 68 in its remote end which may communicate with an internal syringe cavity 70 formed within the neck 60, the conical front wall 58, and the body 54 of the syringe 28. The rear end of the cavity 70 may be further defined by a forward facing surface 72 of a syringe plunger 74. In one particular embodiment, this surface 72 is conical. The conical surface 72 is of a slope which conforms to the slope of the interior of the conical front wall 58. The syringe plunger 74 may be snugly slidable within the body 54 of the syringe 28 such that the cavity 70 is of variable volume.

Referring now to FIGS. 2-4, the syringe plunger 74 can be seen more clearly within the cylindrical barrel of the body 54 of the syringe 28. The syringe plunger 74, when the syringe 28 is attached to the injector 20, is located proximal to and in substantial alignment with the plunger drive ram 46 of the injector 20. The plunger drive ram 46 is driven by a motor to move in a forward or rearward motion along its longitudinal axis of symmetry 76 to deploy the plunger drive ram 46 and thus the syringe plunger 74 in a forward or rearward motion along the axis of symmetry 66 of the syringe 28 to inject fluid into a human or animal subject or fill the syringe 28 with fluid, respectively. For example, one may load a pre-filled syringe into the injector 20 of the present invention, and by deploying the plunger 74 in a forward direction, may thereby expel fluid from the syringe 28. In so doing, the fluid may be injected into the human or animal subject. Alternatively, an empty syringe 28 may be loaded into the injector 20 and deploy the syringe plunger 74 to its forward-most position. Thereafter fluid may be loaded into the syringe 28 by operatively connecting the syringe 28 to a source of fluid and retracting the syringe plunger 74 in a rearward direction in order to pull fluid into the syringe 28.

In general, in the injector system of the present invention, the injector 20 involves single phase injections to deliver fluid such as x-ray contrast agents, flushing solutions, and other media for purposes such as enhancing diagnostic imaging in humans. The injector 20 may include a protocol which may be programmed for a single phase injection. The injector 20 of the present invention also may include a manual X-ray scan delay timer which operates for a maximum period of twenty minutes. The syringe drive system 24 may be electromechanical and the injector 20 may be used either with pre-filled syringes or may be used with empty syringes which may then be filled. In one embodiment, in filling an unfilled syringe with the injector 20 of the present invention, the syringe filling rate is generally in the range of about 1 ml/second to about 8 ml/second. The flow rate during an injection is generally in the range of about 0.1 ml/second to about 6 ml/second. This same flow rate may be used for a flushing fluid. The maximum pressure limit of the injector 20 in one embodiment of the present invention is about 250 psi. The injector 20 of the present invention may be designed to operate within an ambient temperature range of about 15° C. to about 45° C. Further, the injector 20 may be designed to withstand an ambient storage temperature range of about −20° C. to about 60° C. The injector 20 may be designed to operate properly within about 1 hour of being in ambient operating temperatures after being subjected to storage temperatures. Additionally, the injector 20 may be designed to operate up to a relative humidity of about 90%. The injector 20 of the present invention may also include a post-injection readout on an LED display 34, and a safety stop mechanism which provides for an electrical stop when the injection parameters are outside the specification of the injection protocol.

The user-injector interface 30 of the injector 20 of the present invention includes a purge/retract trigger 36 in order to control filling and expelling fluid from the syringe 28 and may include a remote console 44. Programming injections may be controlled by controls 90, such as buttons, on the console 44 and/or the powerhead 22 of the injector 20. A display screen 34 on the powerhead 22 may, in one embodiment, provide information regarding the volume of fluid remaining in the syringe 28. The display screen 34 may also provide information regarding the flow rate at which the injection is proceeding. The user-injector interface 30 may be provided in plastic and/or metal form, or a combination of plastic and metal.

In one embodiment of the present invention, the plunger drive ram 46 may include a first coupling element 80 in order to engage a second coupling element 82 disposed on the syringe plunger 74. This allows the syringe plunger 74 to be coupled to the drive ram 46. Thus, once the syringe plunger 74 has been deployed, the plunger drive ram 46 may be retracted, at the same time retracting the syringe plunger 74 within the cylindrical body 54 of the syringe 28. In one embodiment, and referring to FIGS. 2-4, the coupling between the drive ram 46 and syringe plunger 74 is passive. In the illustrated embodiment, the first coupling element 80 of the drive ram 46 includes a slot 84 on an end of the drive ram 46 most proximal to the forward end 56 of the housing 47 of the injector. This slot 84 sized and shaped to match and receive the second coupling element 82, which may be in the form of a rearwardly-facing extension 88 disposed on the syringe plunger 74. While the slot 84 and extension 88 of the illustrated embodiment are mushroom-shaped, it will be recognized by those of skill in the art that any shape which facilitates coupling may be used. Additionally, while the illustrated embodiment depicts first and second coupling elements 80, 82 that result in a passive coupling, those of skill in the art will recognize that first and second coupling elements that result in an active coupling (one which involves some degree of positive gripping) may be used.

As described previously, the injector 20 of the present invention may receive pre-filled syringes. Alternatively, the injector 20 of the present invention may receive empty syringes which must then be filled prior to injecting fluid into a human or other animal subject. In one embodiment, the injector 20 of the present invention is adapted to receive 125 ml pre-filled syringes, such as the Ultraject syringe, commercially available from Mallinckrodt Inc. of St. Louis, Mo. Such syringes are used for injecting contrast media to a patient. These 125 ml syringes may be pre-filled with varying amounts of fluid, such as 50 ml, 75 ml, 100 ml or 125 ml, for example. However, alternatively, the injector 20 may receive empty 125/130 ml syringes for indications such as coronary angiography. In another embodiment, the injector 20 of the present invention is adapted to receive 130 ml syringes available from Liebel Flarsheim (part no. 600172). In yet other embodiments, the injector 20 of the present invention may receive 50 ml, 75 ml or 100 ml syringes. In yet another alternative embodiment, the injector 20 of the present invention may be adapted to receive syringes of other sizes.

Referring to FIGS. 1-4, the injector 20 of the present invention includes a powerhead 22 which is operatively connected to a power pack 38 including a power supply 40. In alternative embodiments, the injector system can be expanded to include at least one remote console 44 having a console interface 89 to the injector 20, to allow for remote control of the injection. This will be discussed in greater detail below.

Referring now to FIG. 1, the injector 20 of the illustrated embodiment includes a user-injector interface 30 having a plurality of controls 90 which are used to control the operation of the injector powerhead 22. These may include controls including, but not limited to, "start", "stop", "pause", "flow rate increment", "flow rate decrement", "volume increment", and "volume decrement". The powerhead 22 of the injector 20 also may include a display screen 34 to relay information about an injection procedure to an operator. This information indicates to the operator when an injection is enabled and when an injection is in progress. In one embodiment, the display 34 may include two numeric displays, one for displaying volume information and one for displaying flow rate information. In this embodiment, the volume display displays the programmed volume when the injector 20 is in a programming mode, and displays the injection volume when injecting. Similarly, in this embodiment, the flow rate display displays the programmed flow rate when the injector 20 is in a programming mode, and displays the injection flow rate when in injection mode. The injector 20 of the present invention may also include a visual indicator 91 to indicate: (1) when the injector 20 is enabled and ready to inject, (2) when an injection is in progress, and (3) when an injection is complete. Additionally, if the flow rate is reduced during an injection, the visual indicator 91 may signal this as well. Further, if the injector 20 detects an injector 20 fault condition, the visual indicator 91 may signal this information. This visual indicator 91 may appear on the display screen 34 of the user interface 30, or may be separate from the display screen 34. In the illustrated embodiment, the visual indicator 91 may include an LED display.

Referring now to FIGS. 2-6, the combination of the syringe 28 being operatively connected to the injector 20 of the present invention, by way of the syringe mount 26, is more clearly shown. By the arrangement shown, the syringe 28 is inserted into the injector 20 such that a syringe mating system 64, which may be in the shape of a flange circumferential about a distal end of the cylindrical barrel of the syringe 28, communicates with an engaging slot 84 disposed in the forward end 56 of the injector powerhead housing 47. As the syringe 28 is positioned in proximity to the slot 84 and moved downwardly toward the base of the injector 20 so as to be inserted in the slot 84, it engages a first member 92 and a second member 94 which may each be gripping members and may each be movable about a pivot point 96 and are biased toward the longitudinal axis of symmetry 76 of the plunger drive ram 46. In the illustrated embodiment, the gripping first and second members 92, 94 may further include an internal groove 98 disposed in the first and second gripping members 92, 94. This groove 98 may communicate with the slot 84 to thereby form a retention area to aid in connection of the syringe 28 to the injector 20. As the syringe 28 is moved into insertion with the slot 84 and groove 98, the engagement of the syringe 28 with the first and second gripping members 92, 94 of the syringe mount 26 may cause the first and second gripping members 92, 94 to be spread outwardly by the body 54 of the syringe 28 as the syringe 28 slides past the gripping members 92, 94. As the syringe 28 continues to slide into engaging relationship with the injector 20, the biased nature of the first and second gripping members 92, 94 may move them back toward the longitudinal axis 76 of the plunger drive ram 46. Additionally, the force provided by the cylindrical barrel of the body 54 of the syringe 28 against the base of the gripping members 92, 94 facilitates movement of the first and second gripping members 92, 94 toward the longitudinal axis 76 of the plunger drive ram 46. Thus, the first and second gripping members 92, 94 move into gripping relationship circumferentially around the body 54 of the syringe 28 to thereby couple the syringe 28 to the injector 20 in proximity to and in substantially co-axial alignment with the plunger drive ram 46. This alignment allows for subsequent forward translation of the drive ram 46 to express contrast media or other fluid from the cylindrical body 54 of the syringe 28, through the discharge tip 62 of the syringe 28, and into an animal subject, such as a human. The syringe plunger 74 is connected to the plunger drive ram 46 by the first and second coupling elements 80, 82 as described previously.

In the illustrated embodiment of the present invention, the first and second gripping members 92, 94 are diametrically opposite one another, about the axis of symmetry 76 of the plunger drive ram 46, so that the first and second gripping members 92, 94 have circumferential portions on opposed faces 100, 102 that are diametrically opposite one another and exterior to the cylindrical barrel of the syringe 28. Upon attachment of the syringe 28 to the forward end 56 of the injector 20, the first and second biased movable gripping members 92, 94 of the injector 20 engage the side surface of the exterior cylindrical body 54 of the syringe 28, as described above, to hold the syringe 28 in place against and in alignment with the drive ram 46 of the injector 20 of the present invention.

As described briefly above, the syringe mount 26 of the injector 20 of the present invention includes first and second gripping members 92, 94 having opposed faces 100, 102, which are preferably arcuately shaped. In one embodiment, the arcuate opposed faces 100, 102 may further include a metal ridge (not shown) in order to "bite" into the body 54 of the syringe 28 to facilitate gripping of the syringe 28. Alternately, in yet another embodiment, each arcuate face 100, 102 of the first and second gripping members 92, 94 may bear a plurality of ridges of teeth (not shown). Such teeth may be on the first and second gripping members 92 94, or may be included on any metal ridges. The pivotal movement of the first and second gripping members 92, 94 alters the distance between their arcuate faces 100 102, as they pivot toward and away from one another. In the illustrated embodiment, these first and second gripping members 92, 94 are each movable. However, in alternative embodiments (not shown), it is possible to use a single movable member disposed in spaced relation to a nonmovable arcuate stop or abutment toward which the movable gripping member is biased.

The first and second movable gripping members 92, 94 may each be pivotally mounted about shafts or pivot pins 104, which, in certain embodiments may also include bias springs 106 associated with each of the first and second gripping members 92, 94. In such an embodiment, one end of each of the bias springs 106 is in contact with its respectively associated gripping member, and the opposite end of each bias spring 106 seats or bears against portions of the housing 47 of the injector 20. The bias springs 106 are journalled about the pins 104 which form the pivot axes of the first and second gripping members 92, 94.

The first and second gripping members 92, 94 as described above are biased toward the axis of symmetry 76 of the plunger drive ram 46 by the bias springs 106. Stated differently, the bias springs 106 bias the first and second gripping members 92, 94 such that their confronting faces 100, 102 are urged toward each other. In certain embodiments, once the cylindrical body 54 of the syringe 28 is inserted into the syringe mount 26, it cannot be extracted by lifting the syringe 28 away from the syringe mount 26. In fact, any such movement of the syringe 28 away from the syringe mount 26 in such an embodiment of the invention may result in intensified gripping of the cylindrical body 54 of the syringe 28 by the first and second gripping members 92, 94. However, it will be recognized by those of skill in the art that it is not necessary that the gripping intensity of the first and second members 92, 94 is such that any movement intensifies the gripping. Additionally, it will be apparent to those of skill in the art that bias springs 106 are not necessary for the coupling of syringe 28 to injector 20. Rather, in certain embodiments, the positive force of the syringe barrel against the first and second gripping members 92, 94 will retain the syringe 28 within the gripping members 92, 94. In such an embodiment, the syringe 28 is connected to the injector 20 through a friction fit that supplies enough force to retain the syringe 28 during an injection procedure, but which releases the syringe 28 upon positive movement of the syringe 28 away from the injector 20.

It will be appreciated by those of skill in the art that, in alternate embodiments of the invention, first and second gripping members 92, 94 are not necessary for the gripping function. In such alternative embodiments, a single gripping member may be used to grip the syringe, thereby operatively connecting the syringe to the injector. In this alternate embodiment, the gripping member must be of a curved shape and cover enough of the circumference of the syringe when in contact with the cylindrical barrel in order to hold the syringe against the injector. In such an embodiment, each arm extending from the center point of the gripping member has a degree of elasticity such that the arms may splay outwardly and inwardly to allow for the insertion and/or removal of a syringe.

Thus, the various embodiments of the syringe mount 26 of the injector 20 of the present invention, including those using one gripping member and those using more than one gripping member, may include, but are not limited to, the following: (1) a syringe mount 26 that holds the cylindrical barrel of the syringe 28 on a contiguous 210° C. of the syringe circumference; (2) a metal spring clip that allows a contiguous 230° C. contact area with the circumference of the cylindrical barrel of the syringe 28 and provides a sharp edge to bite into the syringe 28; (3) first and second gripping members 92, 94 having opposing faces 100, 102, each contacting 45° C. of the circumference of the cylindrical barrel of the syringe 28 for a total of 90° C. of contact area; (4) first and second gripping members 92, 94, each of the arcuate faces 100, 102 having 80° C. of contact area with the circumference of the cylindrical body 54 of the syringe 28 for a total of 160° C. of contact with the syringe body 54; (5) first and second gripping members 92, 94, each arcuate face 100, 102 having 150° C. of contact area with the cylindrical barrel of the syringe 28 for a total of 300° C. of contact with the syringe body 54. In the illustrated embodiments showing two first and second gripping members 92, 94, the gripping members 92, 94 may include or be made of a metal, such as stainless steel, so they bite into the cylindrical body 54 of the syringe 28.

After a syringe 28 has been operatively connected to the injector 20 by way of the syringe mount 26 such that the axes of symmetry 66, 76 of the syringe 28 and the plunger drive ram 46 are substantially coaxial, a motor of the injector 20 may be used to deploy the plunger drive ram 46 into the syringe cavity 70 to expel fluid from the syringe 28. After advancement of the syringe plunger 74 by movement of the drive ram 46 through the interior cavity 70 of the syringe body 54, the drive ram 46 may be retracted from the distal end of the syringe 28. Once the plunger drive ram 46 is fully retracted, the syringe 28 may be removed from the syringe mount 26 in one embodiment of the injector 20 through the use of a release catch (not shown in the illustrated embodiment) which moves the first and second biased movable gripping members 92, 94 away from and out of engagement with the exterior cylindrical body 54 of the syringe 28. Alternatively, when loading an initially empty syringe into the syringe mount 26 of the injector 20, the plunger drive ram 46 may first be extended into the syringe cavity 70. It may then be retracted in order to draw fluid into the syringe 28. This fluid may then be injected into a subject by once again translating the plunger drive ram 46 in a forward direction. After subsequently retracting the plunger drive ram 46, the syringe 28 may be released by operating the release catch. In an alternate embodiment, the syringe mount 26 may not include a release catch, but rather may connect the syringe 28 to the injector 20 through a friction fit that supplies enough force to retain the syringe 28 during an injection procedure, but which releases the syringe 28 upon positive movement of the syringe 28 away from the injector 20.

Referring now to FIGS. 2-4, the injector 20 of the present invention also features a hand-operated purge/retract trigger 36 which facilitates operator control of the injector 20. The trigger 36 allows a user to purge air from the syringe 28 and to retract the drive ram 46 after an injection. Additionally, the trigger 36 allows a user to dynamically vary the flow rate while injecting or retracting. This aspect of the present invention includes a trigger 36 movable between home, forward, and reverse positions. Movement of the trigger 36 to the forward position causes the injector 20 to move the plunger drive ram 46 forward to expel fluid from the syringe 28, and movement of the trigger 36 to the reverse position causes the injector 20 to move the drive ram 46 in reverse to potentially draw fluid into the syringe 28, or to retract the drive ram 46 from the syringe 28 prior to removing the syringe 28 from the injector 20. The intuitive trigger 36 is designed such that it allows for variable injection speeds and also may include a locking mode which allows for hands free injection.

More specifically, in one embodiment of the injector 20 of the present invention, the trigger 36 is mounted on a pivot 110, and is biased to the home position by at least first and second springs 112, 114 positioned on opposite sides of the trigger 36. Rotation of the trigger 36 away from the home position progressively compresses the springs 112, 114 to an increasing degree at increasing angles of lever rotation. Sensors 116 located in the interior of the housing 47 and associated with the trigger 36 then detect the angle of the trigger 36 so that this angle can be used to control the speed of motion of the plunger drive ram 46. Using this structure and control, the relative position of the trigger 36 can be made proportional to the flow rate of fluid into or out of the syringe 28 which is attached to the injector 20, thereby providing the operator with intuitive feedback on the operation of the injector 20.

The trigger 36 is rotatable on an axis of rotation 118. When the hand operated trigger 36 is left in its home position, no motion of the drive ram 46 is generated by the powerhead 22. However, when the hand operated trigger 36 is rotated toward the syringe 28 (i.e., to forward position), forward motion of the drive ram 46 is generated by the powerhead 22, thereby expelling fluid or air from the syringe 28. Alternatively, when the trigger 36 is rotated away from the syringe 28 (i.e., to a reverse position), reverse motion of the drive ram 46 is generated by the powerhead 22, thereby filling the syringe 28 with fluid or air.

Still referring to FIGS. 2-4, the structure of the injector 20 to allow non-contact control of the injection procedure by use of the intuitive trigger 36 is more clearly shown. The injector 20 of the present invention generally may include a compact modular design facilitating manufacture as a hand-held injector 20 in one embodiment. In particular, control circuitry of the injector 20 of the present invention may be incorporated onto a printed circuit board 120. One feature of the injector 20 of the present invention is the use of magnetic conductors 122 to channel magnetic field energy from magnets 124 positioned in the intuitive trigger 36 through the injector housing 47 and into the vicinity of magnetic sensors 116 operatively connected to the circuit board 120. In one embodiment, by using magnetic conductors 122 to carry magnetic fields through the injector housing 47, circuit board mountable magnetic sensors 116 can be used thereby reducing the overall cost as compared to individually packaged sensors for mounting in an injector housing. The use of such non-contact control also eliminates the need for wiring through the housing 47, thereby enhancing seal integrity.

To determine the direction and degree of rotation of the trigger 36, a plurality of magnets 124 may be disposed on or in the trigger 36, so that rotation of the trigger 36 increases or decreases distances between magnets 124 on the controls of the trigger 36 and in the injection housing 47, creating a changing magnetic field that can be detected by the magnetic sensors 116 associated with the control circuitry of the powerhead 22. In particular, the injector 20 of the present invention may use a Hall-effect sensor in one embodiment. The function of the Hall sensor is based on the principle of the Hall effect: namely, that a voltage is generated transversely to the current flow direction in an electric conductor if a magnetic field is applied perpendicularly to the conductor. In certain embodiments of the invention, since the Hall effect is most pronounced in semiconductors, one suitable Hall element is a small platelet made of semiconductor material. A Hall plate with current terminals and taps for the Hall voltage may be arranged on a surface of the sensor. This sensor elements detect the components of the magnetic flux perpendicular to the surface of a chip and emits a proportional electrical signal which is processed in the evaluation circuits integrated in the circuit board 120. In a particular embodiment of the present invention, the injector 20 includes analog, or linear sensors. Linear Hall sensors generate an analog output voltage which is proportional to the magnetic flux perpendicular through the Hall plate. Thus, the sensors operatively connected to the circuit board 120 of the injector 20 of the present invention can determine from the magnetic flux the degree to which the trigger 36 has been rotated away from the home position, and adjust the electrical output and thus the velocity of the plunger drive ram 46 accordingly.

When the trigger 36 is rotated forward, the sensors 116 associated with the control circuitry detect this rotation from signals produced by the magnetic field, and causes the plunger drive ram 46 to move forward, i.e., outward from the powerhead housing 47, at a velocity proportional to the angle of deflection of the trigger 36 away from the home position. Alternatively, when the trigger 36 is rotated in a reverse direction, the control circuitry detects this rotation from signals produced by the magnetic field, and causes the plunger drive ram 46 to move backward, i.e., into the powerhead housing 47, at a velocity proportional to the angle of deflection of the trigger 36 away from the home position.

As described above, the power injector may also include first and second springs 112, 114 associated with the control trigger 36 which engage the housing 47 of the injector 20 and produce torque tending to return the shaft to the home position. When the trigger 36 is in its home position, the springs 112, 114 apply opposing torques to the trigger 36, tending to hold the trigger 36 in the home position. In this position, the sensors 116 produce a signal indicating that the trigger 36 is in the home position. In this position, the control circuit of the powerhead 22 can determine that no motion of the drive ram 46 is being requested through hand operated movement control of the trigger 36.

When the trigger 36 is rotated away from the home position, the sensors 116 produce a signal, which may be an analog signal, indicating that the trigger 36 is away from the home position. As this occurs, the control circuit may read the signal produced by the magnets 124 to determine the position of the trigger 36 and produce the appropriate motion of the plunger drive ram 46.

As previously described, the velocity of motion of the plunger drive ram 46 is proportional to the extent of the movement or rotation of the trigger 36 away from the home position. As this occurs, the mechanical structure of the first and second springs 112, 114 insures that a return torque is being applied to the trigger 36 as the trigger 36 is rotated to increasing angles away from the home position. Depending on the stiffness of the springs 112, 114 and the range of motion of the trigger 36, this return torque may be approximately equal at all deflection angles, or may increase or decrease over increasing and decreasing deflection angles. An increasing return torque compared to the deflection angle may provide the operator with additional feedback on the velocity of the drive ram 46. Additionally, and as described above, the first and second springs 112, 114 also offer a degree of tension to bias the trigger 36 in the home position. This assists in preventing accidental deflection of the trigger 36 away from its home position when it casually abuts another object, such as when the injector 20 is laid down on a table.

Additionally, the injector 20 may include other mechanisms to ensure that the trigger 36 is not accidentally displaced from the home position. In certain embodiments, the trigger 36 may be designed so the user has to intentionally enable the trigger mechanism to operate the injector 20.

As described above, when filling a syringe 28 or discharging the contents of a syringe 28, there may be an ideal maximum speed at which fluid can be drawn into the syringe 28 and expelled from the syringe 28 due to safety considerations. Additionally, any such optimal injection flow rate may be dependent on the particular procedure and/or the fluid to be injected. To control the filling and discharge of fluid from syringes, and to maintain the safety of those involved in the injection procedure, the operator should have feedback as to when an ideal speed has been reached, so that syringes can be filled or discharged at this optimal speed. Additionally, the injector 20 may include a mechanism to prevent the discharge of fluids above certain speeds. One purpose of the first and second springs 112, 114 described above is to provide the operator with mechanical feedback of the angle of deflection of the trigger 36, which may correspond approximately to the ideal fill speed. More specifically, the control circuit of the powerhead 22 may establish that the plunger drive ram 46 will move near to the ideal speed when the trigger 36 has been rotated to a certain position. Accordingly, an operator wishing to fill a syringe 28 at the ideal speed, can rotate the trigger lever until the increasing torque is noted and then hold the trigger lever at that location to fill the syringe 28.

Additionally, the injector 20 of the present invention may include a speed lock associated with the trigger 36 of the injector 20. This speed lock allows an operator to program in and inject or retract the drive ram 46 at a particular flow rate.

This injection may occur at a particular flow rate regardless of the extent to the depression of the trigger 36 itself or, alternatively, may be programmed to inject at a particular flow rate unless that program is overridden by a change in the deflection of the trigger 36. In one embodiment, the trigger speed lock may be located on the control panel of the injector 20. It operates to lock in the current speed of the drive ram 46, whether retracting or injecting, when the speed lock is activated. In one particular embodiment of the injector 20 of the present invention, any plunger drive ram 46 movement may be halted when any other control 90 or the trigger 36 itself is depressed while the lock is active. While in the illustrated embodiment, it is noted that the controls for the trigger speed lock are located on the injector powerhead 22, it will be appreciated by those skilled in the art that the speed lock controls may be located on the remote console 44, or any other component of the injector system.

In certain embodiments, the injector 20 of the present invention may be enabled to allow the speed lock feature to be activated while expelling contrast media or other fluid from a syringe 28 associated with the injector 20. If the injector 20 is speed locked on a particular flow rate, and any of the powerhead 22 switches are activated, or the purge/retract trigger 36 is reactivated, the injector 20 may be designed to unlock the flow rate and run at the flow rate determined by the purge/retract trigger 36. Additionally, when retracting, the injector 20 may activate the flow rate speed lock feature when the purge/retract trigger 36 is fully engaged in the retract direction for a minimum period of time, such as for two seconds. When retracting and the flow rate speed lock is activated, the injector 20 may be deactivate the speed lock if the purge/retract trigger 36 is reactivated or the injector ram reaches its home position.

Referring to FIGS. 2-6, the injector 20 of the present invention also includes a structure to prevent rotation of the drive ram 46. This prevents the drive ram 46 from rotating about its axis of symmetry 76 during an injection procedure. The anti-rotation of the drive ram 46 is achieved by the shape of the drive ram 46 itself. In the illustrated embodiment, a cross-section of the drive ram 46 taken perpendicular to the axis of symmetry 76 of the drive ram 46 is in the shape of back to back "D"s, having a first flat surface 126 across the top of the ram, a second flat surface 128 across the bottom of the ram and two curved surfaces 130, 132, one on each side of the ram 46. This drive ram 46 inserts through a similarly shaped orifice 134 in a plate 136 located in the forward end 56 of the housing 47 injector 20 of the present invention nearest the syringe 28. During movement of the drive ram 46 in either forward or reverse directions, the drive ram 46, at all times, remains disposed through the similarly shaped orifice 134 in the plate 136. The orifice 134 in the plate 136 is sized such that the drive ram 46 may move freely within the orifice 1 but will cause the drive ram 46 to abut the edge of the orifice 134 should the drive ram 46 begin to rotate about its longitudinal axis 76. In the illustrated embodiment, due to the flat surfaces 126, 128 on the top and the bottom of the drive ram 46, the ram 46 is thus unable to rotate as it moves forward. This is important in keeping the first coupling element 80, disposed at the forward end 56 of the drive ram 46, properly aligned, such as in an upward facing direction, so that syringes 28 may be removed and replaced into the injector 20. While the illustrated embodiment depicts a back-to-back "D" shape, those of skill in the art will recognize that other shapes may be used.

The injector 20 of the present invention also includes a ram home detector 50 which operates to determine whether an end of the drive ram 46 is proximal to the forward end 56 of the injector housing 47. This position is the "home" position of the drive ram 46. The ram home detector 50 accurately detects both when the drive ram 46 is a certain distance from the home position (such as ½ inch) and when the ram 46 is at the home position. This detection may be achieved through the use of magnets 138. This allows the elimination of secondary analog position devices, such as a potentiometer. For example, a magnet 138 may be disposed on the surface of the drive ram 46 and a magnetic sensor 140 may be positioned in the housing 47. The magnetic sensor 140 can detect a magnetic field produced by the magnet 138. This magnetic field will increase in intensity as the magnet 138 on the drive ram 46 approaches the sensor 140. The intensity of the magnetic field can be calibrated to determine when the drive ram 46 is at its home location.

As described above in the background of the invention, many present injectors use potentiometers and/or encoders on the motor as redundant systems to track the location of the drive ram of an injector. The injector 20 of the present invention does not include such a system. Rather, the injector 20 of the present invention includes a magnet 138 disposed on the ram that interacts with sensors 140 along the inner part of the injector 20 to detect the location of the ram 46. When reversing the ram 46 to its home position, for example, this allows the ram 46 to run quickly in reverse mode until it is a certain distance from its home position. During its operation, the injector 20 of the present invention calibrates a value which it assigns to the ram 46 when the ram 46 is in its home position flush with the outer edge of the forward end 56 of the injector 20. In this way, the ram 46 can be run and reversed such that it always comes to a rest in the same home position. This is necessary in being able to remove and replace various syringes, into and out of the drive ram 46, when in the correct location. Thus, when in reverse mode the injector 20 may reverse the ram 46 at a relatively rapid rate until it recognizes that it is close to the home position. The rate of reversal of the ram 46 is then slowed until the injector 20 recognizes that it has reached the pre-calibrated home position. Movement of the ram 46 is then halted such that syringes 28 may be removed from and/or inserted into the injector 20.

Referring now to FIGS. 7, 7A, 8, and 8A, the injector 20 of the present invention may also include a warming cradle 48. In the illustrated embodiment, this warming cradle 48 includes an annular plastic section 142 and a molded plastic base 144. In one embodiment (FIG. 1A), this warming cradle 48 may be integral with the injector 20 such as by extending from the forward end 56 of the housing 47 of the injector 20. In an alternative embodiment, the warming cradle 48 may be part of a hanger 146 to which the injector 20 and syringe 28 are operatively connected prior to starting an injection procedure. The plastic section 142 may extend from the hanger 146 in such a manner as to be disposed proximally to and in confronting relationship with the syringe 28 when the syringe 28 and injector powerhead 22 are operatively connected to the hanger 146 and warming cradle 48. The plastic section 142 of the warming cradle 48 includes a filament of wire 148 which generates heat when an electrical current is driven through it via a suitable electric power source. The filament 148 may extend throughout the region of an annular portion of the plastic section 142 which is in contact, or in confronting relationship, with the syringe 28 and/or pressure jacket, and terminates at either end in electrical leads (not shown) which may be encased in an insulating cable (not shown) which can be operatively connected to the control circuitry of the powerhead 22. Such connection may occur directly through an aperture in the housing 47 of the powerhead 22, or may occur through electrical contacts disposed on the exterior of the powerhead housing 47 which contact electrical contacts disposed on the exterior of the cradle 48 or hanger 146. When current from the powerhead 22 is forced through the leads in the cable and through the filament 148, the filament 148 generates an even heat which warms fluid inside the syringe 28, or maintains the temperature of fluid in a pre-warmed syringe 28. Those having skill in the art will recognize that any alternate, suitable method of generating heat in the warming cradle 48 may be used.

Figure 9:
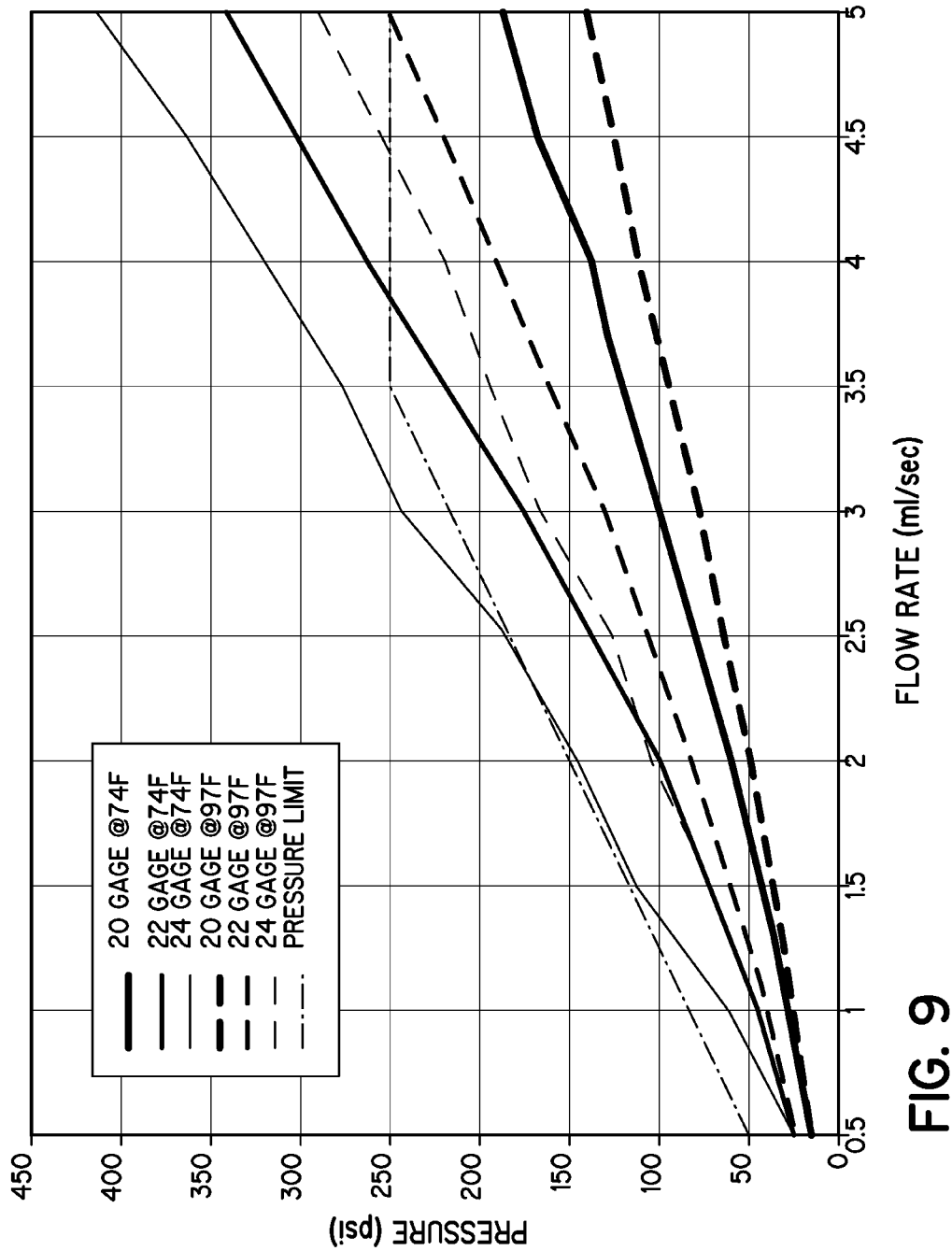
FIG. 9 is a graph demonstrating the limits of pressure versus flow rates in the injector of the present invention.

As described above, and referring to FIG. 9, the present invention also allows for limitation of the pressure supplied by the injector 20. Since low flow rates require less pressure, the injector 20 of the present invention automatically assigns the pressure limit based on the flow rate. The pressure limit value is thus high enough to achieve the programmed flow rate under normal conditions, but won't allow high pressure to develop in the event of unexpected restriction or blockage within the syringe 28 or tube or access port. By automatically assigning a pressure limit based on the flow rate, an operator does not need to remember to alter the pressure limit each time the injector 20 is used. Thus, the injector 20 is able to deliver media at desired rate, but does not allow too much reserved pressure to build in the event that a blockage occurs. This increases the safety of the injector 20 of the present invention over that of injectors of the prior art.

In use, a user may program a flow rate into the injector 20. However, if that flow rate would exceed the pressure limit of the injector 20, the flow rate would be decreased and/or the injection halted for safety purposes. Thus, the injector 20 of the present invention further includes a stop circuit to terminate the injection if the fluid injection pressure exceeds a predetermined limit. Alternatively, the stop circuit may terminate the injection when the fluid injection pressure exceeds a predetermined limit for a predetermined period of time.

In one particular embodiment of the present invention, the predetermined pressure limit is 250 psi. The injector 20 may be designed so that the user cannot adjust the pressure limit function. The pressure limiting function may thus be internally programmed and set prior to injecting. In one embodiment, the pressure limit may be based on the flow rate selected by the user as specified in the equation: Pressure Limit (psi)=(78)(selected Flow Rate ml/s)+50. If the selected flow rate exceeds 2.5 ml/s, the pressure limit may be fixed at a maximum of 250 psi. If the injection pressure approaches the pressure limit, the injector 20 may reduce the flow rate as necessary to keep the injection pressure from exceeding the pressure limit.

As discussed above, in one embodiment as depicted in FIG. 1, the injector 20 of the present invention may include an optional remote console 44 for operating injection procedures by remote control. The remote console 44 is an accessory that connects to the power pack 38 and may be used to monitor and control an injection from a remote location, such as a control room. The user can program, start, stop, and resume an injection as well as dynamically adjust the flow rate while an injection is in progress, all from the remote console 44. The remote console 44 may also contain a timer on the user-console interface 45 for displaying the elapsed time from the start of an injection until the ram is retracted. The timer is present to assist the user in determining when to start an x-ray scan after injecting to achieve optimal image contrast. Thus, a functional remote console 44 for the injector 20 of the present invention may generally be a chargeable console 44 having features and abilities including, but not limited to: (1) starting the injection, (2) stopping or pausing the injection, (3) setting and changing the injection parameters, and/or (4) providing a timer that can be started at the onset of an injection to time the injection. In one embodiment, this timer will have a minimum duration of twenty minutes. However, those of skill in the art will recognize that a timer of any particular minimum duration may be used.

Figure 1A:
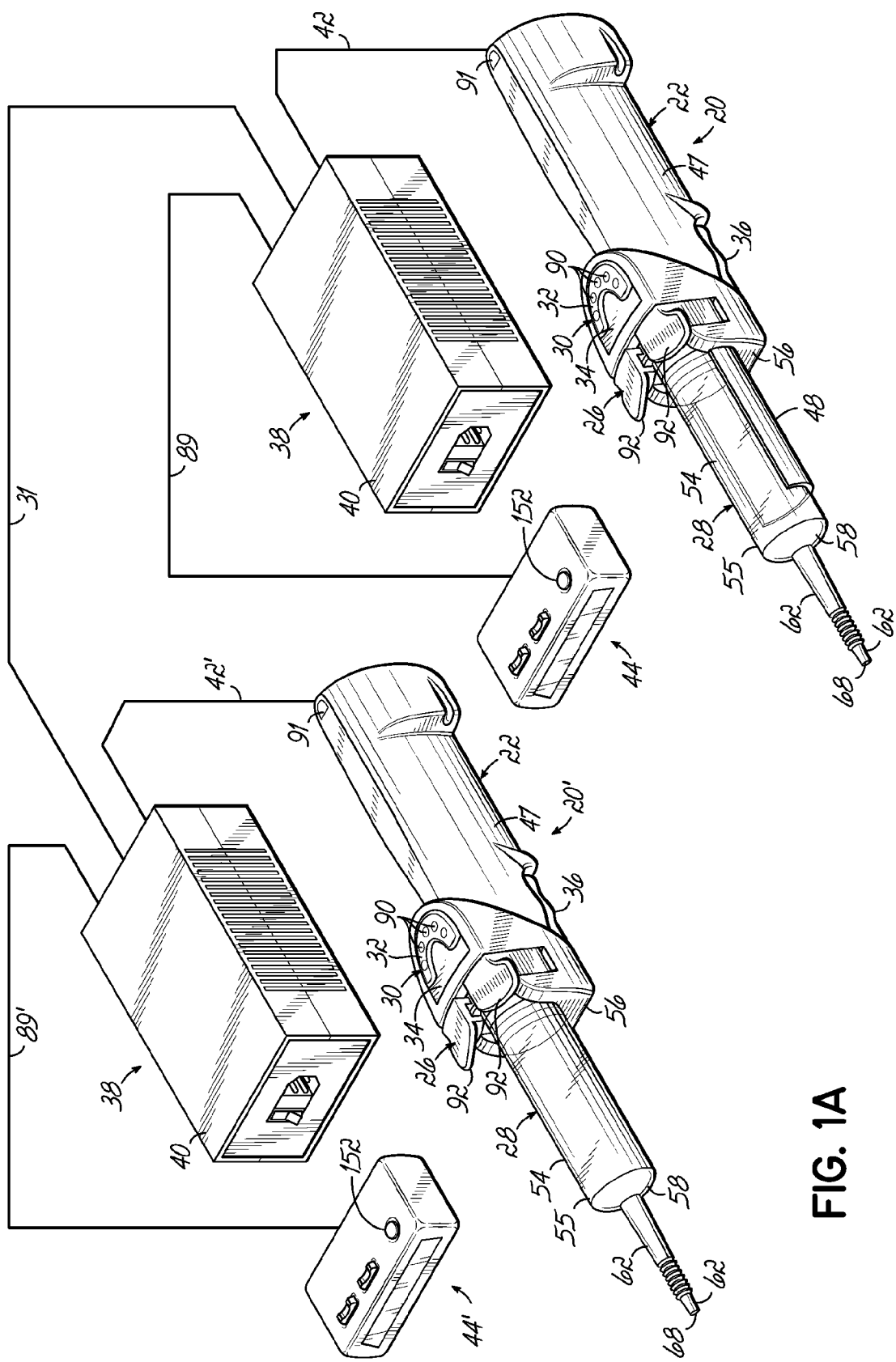
FIG. 1A is a perspective view of an embodiment of the present invention including two injectors, two remote consoles, and two power supplies.
Figure 8A:
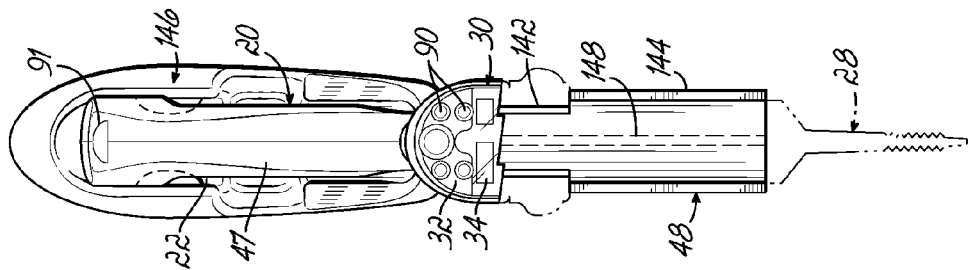
FIG. 8A is a perspective view of the injector of the present invention including a hanger and warming cradle with a syringe attached to the injector and associated with the hanger and warming cradle.
Figure 8:
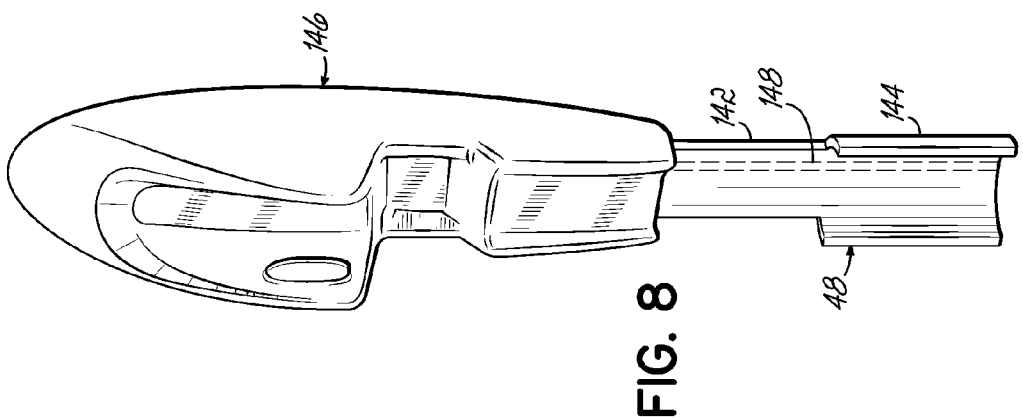
FIG. 8 is a perspective view of the hanger and warming cradle of the injector in accordance with the principles of the present invention.
Figure 7A:
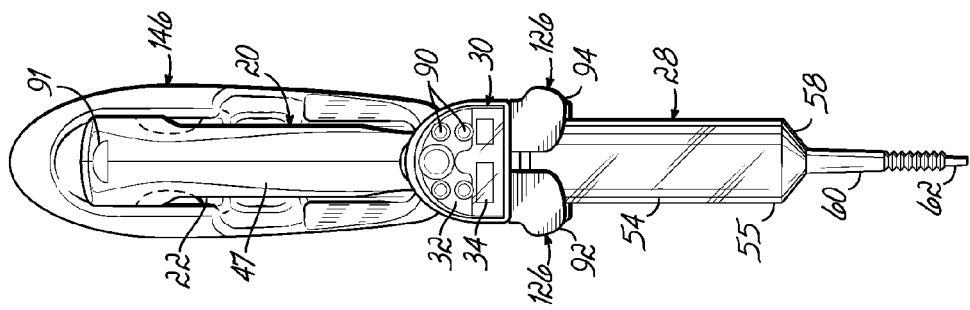
FIG. 7A is a perspective view of the injector of the present invention, including a hanger with a syringe attached to the injector and associated with the hanger.
Figure 7:
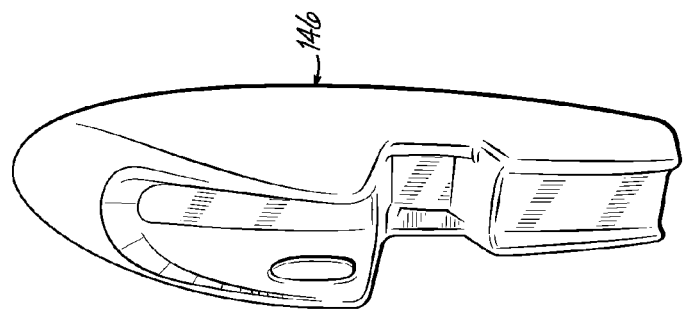
FIG. 7 is a perspective view of the hanger of the injector in accordance with the principles of the present invention.

Also in an alternate embodiment and referring to FIG. 1A, a second injector 20' can be added to an injection system via an optional interface cable. The first and second injectors 20, 20' can then be configured to communicate with one another in order to provide a saline push or to provide for a larger volume injection capability. In this embodiment, the first and second injectors 20, 20' can be configured to communicate in order to provide a saline push or a larger volume capability. This is because, often, injection procedures will require a greater volume of fluid to be injected than is contained by a single syringe 28. Additionally, during certain injection procedures, it may also be desirable to follow an injection with a saline push which may be used to ensure that the entire injection has been received by a subject. When both units are ready to inject, the second injector 20' may be programmed to inject at the completion of the injection of the first injector 20. In this embodiment, a second remote console 44' that connects to a second power pack 38' may be added to facilitate remote control of the second injector 20'. A second power-injector interface 42' and a second console-power interface 89' may be used to interconnect these devices.

A power supply 40 may be connected to the injector 20 through a power-injector interface 42, which may include an extension cable connected via prefabricated connectors. An alternate connection may be provided to allow such an injector extension cable to be shortened to facilitate installation in a particular location while avoiding excess wiring or cable, which may create a safety hazard. In one embodiment, and as used, a 10' coiled cable with connectors at both end, may connect the powerhead 22 to a wall plate (not shown). A 75' extension cable may connect between the wall plate and the power pack 38. This extension cable, in one embodiment, may be a plenum type cable. The connection at the power pack 38 for the 75' extension cable may incorporate a connection scheme that allows the extension cable to be shortened to facilitate a neat installation. The power supply 40 includes a console-power interface 89 in order to communicate with any remote console 44. In one particular embodiment of the present invention, the power supply 40 senses a line voltage during the powerup phase and automatically configures for voltages ranging from about 100 VAC to about 240 VAC, plus or minus about 10% at about 50 HZ to about 60 HZ, plus or minus about 3 HZ. A 10' Ethernet type cable with RJ-11 type connectors may be used to connect the power pack 38 to the remote console 44

The present invention also may include a method for controlling DC power to the injector powerhead 22 and/or remote console 44. In this embodiment of the present invention, a start injection wire may be used to turn on the power and a two-wire serial communication may be used to turn off the power.

As described above in the background of the invention, in previous injectors, generally including a power supply 40, a powerhead 22 and a remote console 44, the remote console 44 generally includes a low-voltage on/off switch. This switch generally includes wires connected to the power pack 38 to control DC power (generally 24 volts) to the console 44 and the powerhead 22. The DC voltage in the power pack 38 may always be present as long as a main power switch is on. The connector size in the console 44 of the larger injectors described in the background of the invention is generally at a minimum 15 pins, and thus these connectors allow for dedicated wires for the power on/off function. However, due to the physically smaller size of the console 44 for embodiments of the injector 20 of the present invention, the connector may generally include only 8 pins. This 8 pin configuration does not allow for any extra dedicated wires for the separate power on/off function on the console 44.

Figure 10:
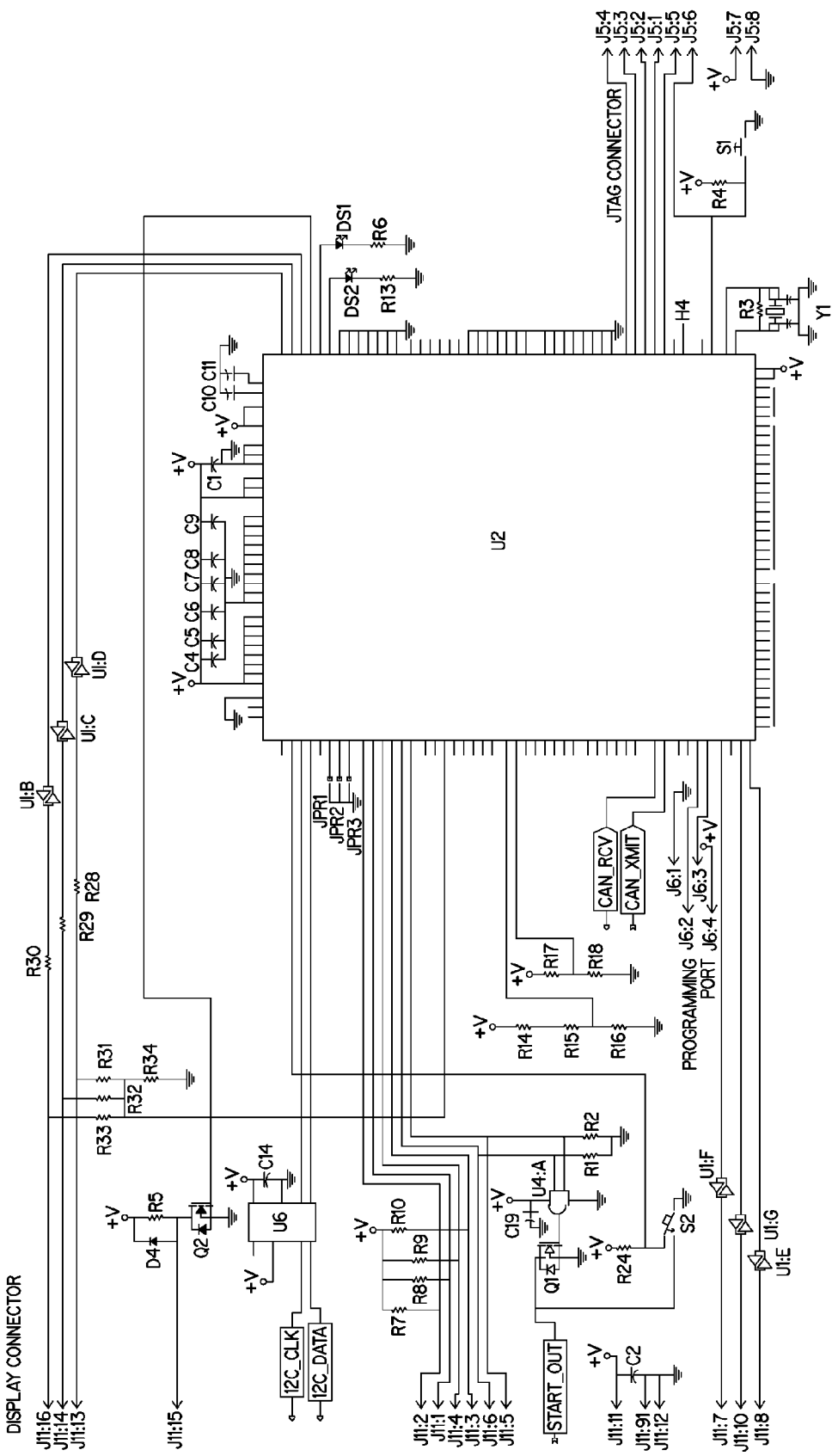
FIG. 10 is a schematic of the control board of the remote console in accordance with the principles of the present invention.
Figure 11:
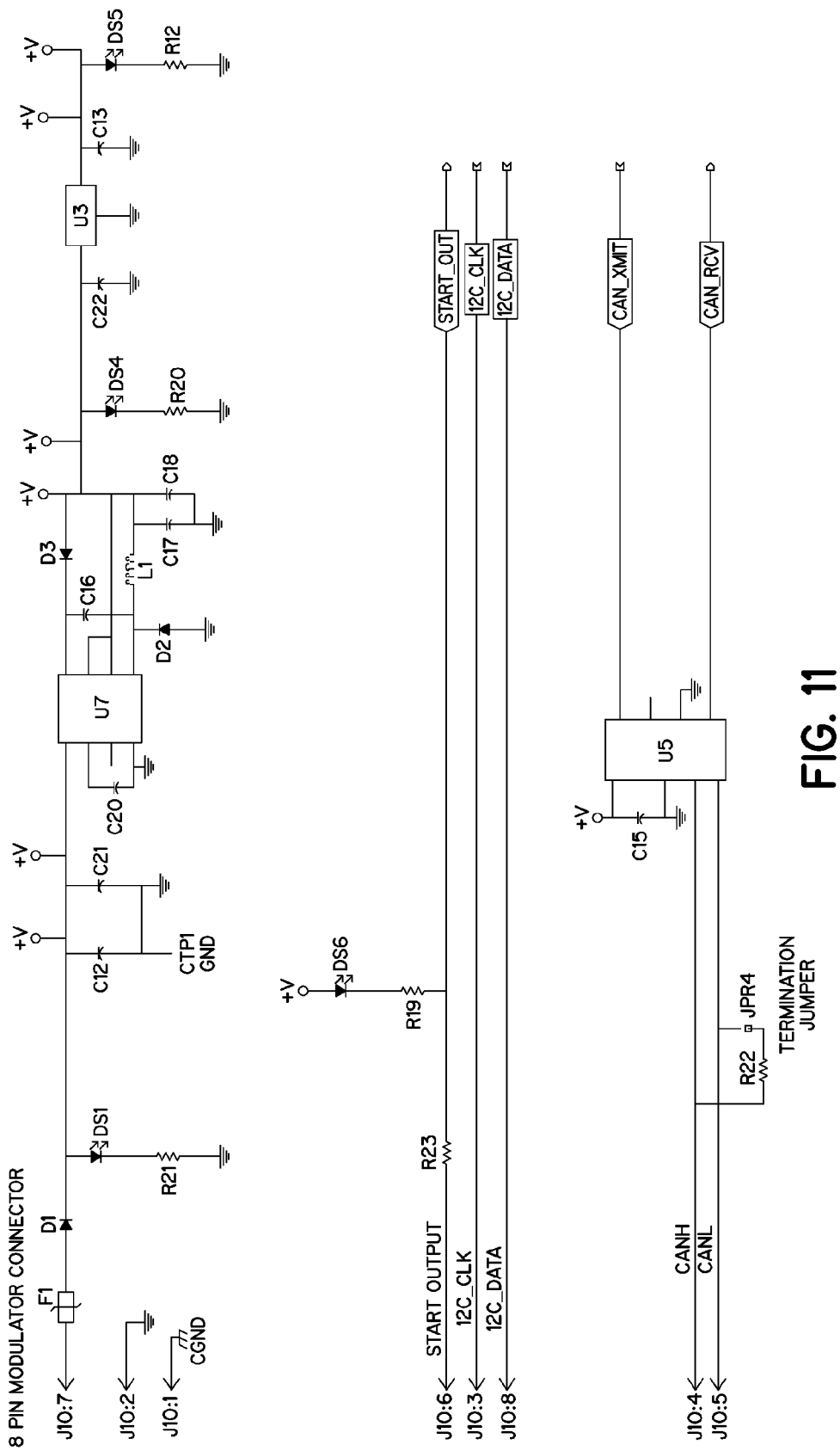
FIG. 11 is a schematic of the control board of the remote console in accordance with the principles of the present invention.
Figure 12:
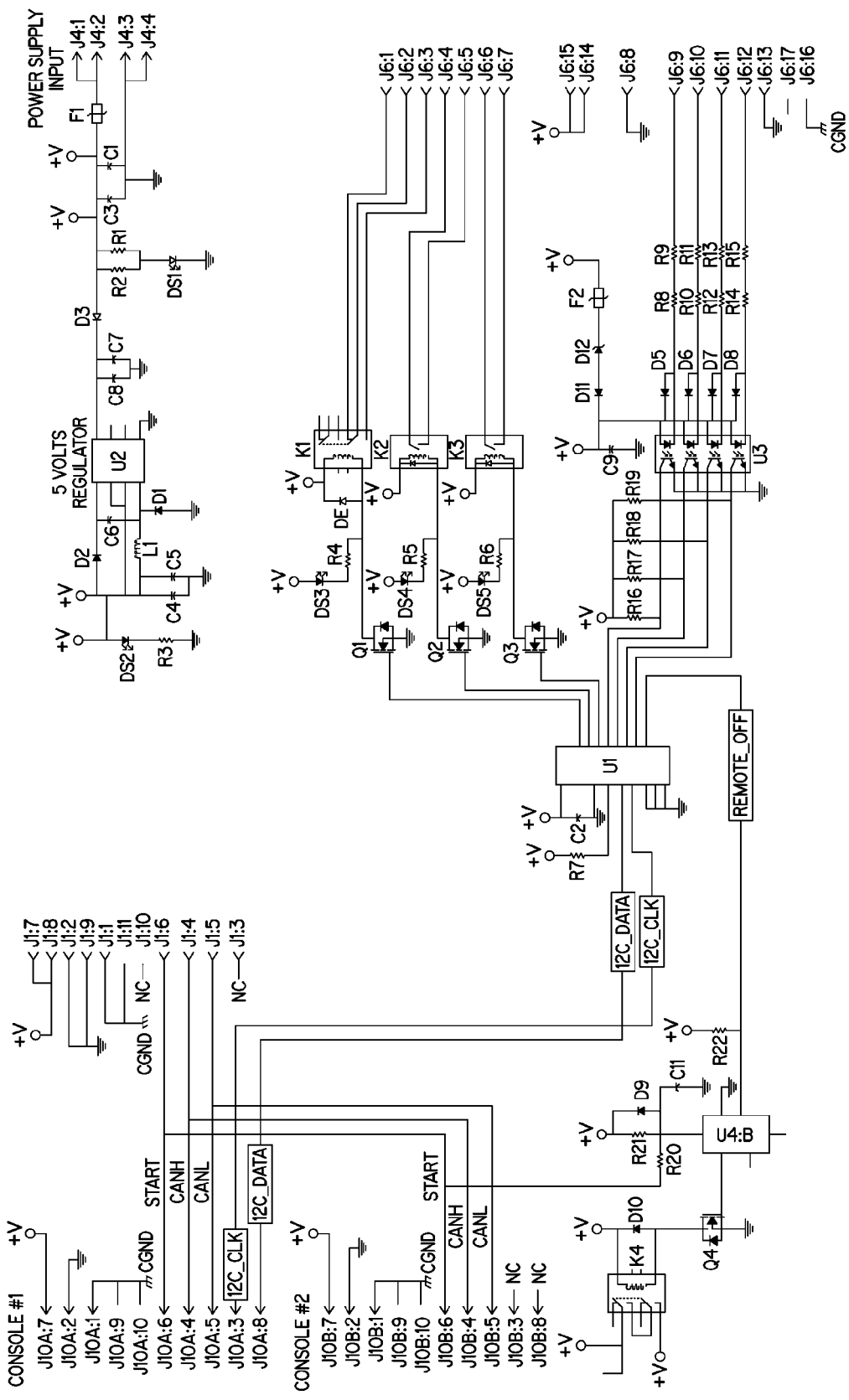
FIG. 12 is a schematic of the power supply interconnect board in accordance with the principles of the present invention.

In view of the above, and referring now to FIGS. 10-12, the separate "soft" power on/off switch may be provided on a remote console 44 as follows. As described above the basic elements of the injector 20 are the powerhead 22, the power pack 38, and the remote console 44. The powerhead 22 is the primary device, needing a supply of generally about 24 volts to function as a stand-alone injector. The remote console 44, as described above, includes the same controls and displays as the powerhead 22 but further includes an injection timer 152 (such as may be used for manually starting a CT scanner) and an on/off switch. The power pack 38 includes a 24-volt power supply 40 as well as an injector to injector interface and a power on/off control. In the particular embodiment of the present invention, the injector to injector interface and on/off circuitry is only functional when a remote console 44 is attached to the system and uses an I2C serial interface to control these features. The powerhead 22 and the console 44 may communicate by a serial communication referred to herein as Controller Area Network (CAN). This CAN communication is used for real time control between the powerhead 22 and console 44. As a redundant system in running an injection, the interconnecting cabling may include a wire which allows all the devices to identify that a start command has been activated from the console 44. In such a configuration, this injection signal must be supported by the CAN interface. If it is not supported, it will be ignored or reported as an error to the remaining components of the injection apparatus and no injection will occur.

In use and in reference to FIGS. 10-12, the communication may operate as follows. For purposes of the following description, one may assume that the main power switch of the power pack 38 is "on" and that 24 volts are present in the power pack 38. Activation of the remote on/off switch will connect a "start out" signal to ground. This wire will turn on the 24 volts for the system power when it is switched to ground. The circuitry used to implement this is flip-flop U4:B, transistor Q4 and relay K4. The remote on/off switch in the console 44 is the only component that can activate this line when the system power is off. When the system power is on, the console 44 start switch and the remote on/off switch may activate this line, which will attempt to turn on system power that is already on. When this happens, no change occurs.

When the system power is on and the remote on/off switch is activated, the remote switch will attempt to turn on the power but at the same time it sends a start signal to the powerhead 22 (which will be ignored) and a signal to the console microprocessor. The software in the processor will wait until the switch depression ends, then delay an appropriate amount of time (in general less than one second). After the delay, the processor sends a power off serial command to the I2C Parallel I/O chip which will toggle the flip-flop U4:B and consequently turn off the system power through K4. If the powerhead 22 or second console are to be used to turn off the power, such a command should be requested through the CAN interface to the first console 44.

The display screen 34 on the injector 20 relays all information regarding the injection procedure to an operator. These parameters include the program flow rate, the real time flow rate for injection while the injection is running, a program volume, the remaining available volume when the injection is running, and a timer to count up from the start of injection to display up to 19 minutes and 59 seconds. This timer will reset when the drive ram 46 is pulled back or after 20 minutes.

The powerhead 22 of the injector 20 of the present invention includes software which, in one embodiment, includes four modes of operation: (1) a manual mode, (2) an auto-inject mode, (3) a syringe size selection mode, and (4) a manufacturing mode. The powerhead 22 also includes a power-on self-test (POST), to check for proper injector operation, and a safe state which the powerhead 22 can enter in the event of serious injector malfunction. When power is applied, the powerhead 22 of the injector 20 of the present invention performs an initialization of the microcontroller and system resources. After this initialization, the powerhead software automatically runs a POST. If the powerhead 22 passes all POST tests, the software then may check for the manufacturing mode. The powerhead software enters the manufacturing mode only if the user activates the volume increment and volume decrement at the same time while the software version number is displayed. If the user alternatively activates the purge/retract trigger 36 while the powerhead software is displaying the software version number, the software proceeds automatically into manual mode.

The powerhead software is equipped to perform a POST of the microcontroller CPU. Following that first self-test, the POST may perform a cyclical-redundancy check (CRC) test of the program Flash Program Read Only Memory (PROM), a CRC test of the data Flash PROM, and a memory test of all data and program RAM. Following those tests, the POST may perform a test of all peripherals internal to the microcontroller which may be used during operation of the injector 20 of the present invention. The POST then may illuminate all visual indicators, including all digits and segments in the LED displays for a minimum of three seconds. Further, the POST may check the power supply voltages for the +24 volt+/−4 volt and +5 volt+/−0.5 volt power supplies. The POST also may check for proper motor cutout relay operation and may check the calibration voltage of all purge/retract trigger sensors 116 to be within +/−0.2 volts. The POST may also activate an audible enunciator for a minimum of 500 milliseconds. The POST also detects whether or not an external start signal is active. If the POST detects an external start signal as being active, the software displays a code indicating an active external start signal and stays in the POST mode until that external start signal becomes inactive.

Upon completion of the POST, the powerhead 22 of the injector 20 of the present invention sends the self-test status to the remote console 44. Upon successful completion of the POST, the powerhead software displays the current software version on the display 34 for a minimum of three seconds. After displaying the powerhead software version number, the powerhead software checks the sensor 140 of the ram home detector 50 to verify that the ram 46 is fully retracted. If the sensor 140 indicates that the ram 46 is not at the home position, the powerhead software then allows the ram 46 to move in the retract direction only and at the same time displays alternating dashes on all digits of the seven segment LED displays. These alternating dashes will continue to be displayed until the ram 46 is moved to the home position. If any of the self-tests fail, the powerhead software transitions to the safe state.

As described briefly above, the powerhead software contains a manual mode. In this manual mode, the software allows the user to program a volume and flow rate for an injection. When entering the manual mode, the powerhead software will recall and display the previously programmed flow rate and volume.

The user interface 30 of the powerhead 22 includes a control panel keypad 32 which may include a volume increment push button and volume decrement push button for programming the injection volume. In one embodiment, the user activates and releases the volume increment button, the powerhead software increments the volume 1 ml. When the user activates and holds the volume increment button, the powerhead software increments the volume 1 ml at a rate of 1 ml per 0.5 seconds+/−0.1 seconds. If the user holds the volume increment button for more than 3 seconds, the powerhead software increments the volume 1 ml at an accelerating rate. If the user holds the volume increment button and the maximum volume is reached, the powerhead 22 holds the program volume at the maximum value and gives an audible beep. If the user holds the volume decrement button and the minimum volume is reached, the powerhead 22 holds the program volume rate at the minimum value and gives an audible beep. The volume decrement button may operate in the same way as the volume increment button except it decrements the program volume. If a 125 ml syringe size is selected, then the program volume ranges from 125 ml down to 1 ml. If the 100 ml syringe size is selected, the program volume ranges from 100 ml down to 1 ml. This programming volume may alternate, depending on the syringe size selected for the powerhead 22. The powerhead software will not allow the user to program more volume than the maximum programmable volume. The maximum programmable volume will be determined to be the syringe size volume or the remaining volume, whichever is less. If a user attempts to program more volume than the maximum programmable volume, the powerhead software will hold the display volume at the maximum programmable value and give an audible beep.

The control panel keypad 32 of the powerhead 22 may include a flow rate increment push button and a flow rate decrement push button for programming the injection flow rate. In one embodiment, when the user activates and releases the flow rate increment button, the powerhead software may increment the flow rate 0.1 ml/s. When the user activates and holds the flow rate increment button, the powerhead software may initially increment the flow rate 0.1 ml/s and hold for 1 second. If the user continues to hold the flow rate increment button, the powerhead software may increment the flow rate 0.1 ml/s at a rate of 0.5 seconds. If the user holds the flow rate increment button for more than 4 seconds, the powerhead software may increment the flow rate 0.1 ml at an accelerating rate. The flow rate decrement button may operate in the same way as the flow rate increment button except it decrements the program flow rate. The powerhead 22 may allow the programmed flow rate to range from 6.0 ml/s down to 0.1 ml/s. If the user holds the flow rate increment button and the maximum flow rate is reached, the powerhead 22 may hold the program flow rate at the maximum value and give an audible beep. If the user holds the flow rate decrement button and the minimum flow rate is reached, the powerhead 22 may hold the program flow rate at the minimum value and give an audible beep.

The powerhead software may enter a pre-filled syringe selection mode if the injector 20 is in manual mode and the user activates and holds the volume increment button for more than 3 seconds when the volume displayed is at the maximum programmed volume. When entering the pre-filled syringe selection mode, the powerhead software may continually flash an indicating signal, such as "PF", at the slow rate in the flow rate display, and display, without flashing, the pre-filled syringe sizes in the volume display. The "PF", or other indicating signal, is to inform the user that the injector 20 is in the pre-filled syringe selection mode. The fast flash rate, in one embodiment, may be 750 ms on and 250 ms off. When entering the pre-filled syringe selection mode, the powerhead software may display the previously selected syringe size in the volume display. The powerhead software may allow the user to increment to the next larger syringe size by activating the volume increment button. The syringe size may increment to the next larger syringe size for each activation of the volume increment button. The selectable syringe sizes may be 50 ml, 75 ml, 100 ml, 125 ml, and 130 ml. The powerhead software may ignore further syringe size increments when the largest syringe size is displayed. If the user activates the volume decrement button, the powerhead software may decrement the syringe size to the next smaller size. The syringe size may decrement to the next smaller size for each activation of the volume decrement button. The powerhead software may ignore further syringe size decrements when the smallest syringe size is displayed. The powerhead software may select the displayed syringe size and exit from syringe size selection mode and transition to the manual mode if the user: (1) activates the flow rate increment or decrement push-button, (2) activates the start push-button, (3) activates the purge/retract trigger 36, or (4) opens and closes the syringe mount 26. The powerhead software may have a syringe size selection mode time-out feature wherein after 10 seconds of inactivity, the software may select the displayed syringe size and exit to the manual mode. When exiting from syringe size selection mode, the software may store the selected syringe size in non-volatile memory.

As described above, the powerhead 22 contains a purge/retract trigger 36 to allow the user to vary the flow rate when purging air from the syringe 28 or to retract the ram 46 after an injection. The powerhead software may activate the injector motor in the "expel" direction if the purge/retract trigger 36 is activated in the expel direction. When the purge/retract trigger 36 is activated in the "expel" direction, the powerhead software may decrement the volume display 1 ml for every 1 ml of fluid expelled. The powerhead software may activate the injector motor in the "retract" direction if the purge/retract trigger 36 is activated in the retract direction. When the purge/retract trigger 36 is activated in the "retract" direction, the powerhead software may increment the volume display 1 ml for every 1 ml that the ram 46 is retracted. The powerhead software may control the flow rate in proportion to the distance to which the user displaces the trigger 36 away from its home position. The powerhead software may not move the injector ram 46 when the purge/retract trigger 36 is in the home position.

The powerhead software may adjust the range of the purge/retract trigger 36 so that the maximum achievable flow rate may be limited to the user programmed flow rate or the flow rate allowed when the pressure is being limited. For example, if the user programmed a flow rate of 2.0 ml/s, the injector 20 should adjust the range of the purge/retract trigger 36 so that a flow rate of 2.0 ml/s is achieved when the trigger 36 is fully engaged in the forward direction. If the user programmed a flow rate of 3.5 ml/s, then the injector 20 should adjust the range of the purge/retract trigger 36 so that a flow rate of 3.5 ml/s is achieved when the trigger 36 is fully engaged in the forward direction. When the purge/retract trigger 36 is fully engaged in the forward direction, the software may control the injector motor to deliver the maximum achievable flow rate. The powerhead software may correlate the flow rate to the purge/retract trigger 36 position as shown in Table 1. The position tolerance may be +/−2% of fully engaged.

TABLE 1

| Flow Rate (ml/s) | % of Fully Engaged |
| --- | --- |
| 0 | 0 to 12 (Dead Band) |
| 0.1 to 0.5 | 12 to 50 |
| 0.6 to Programmed Flow Rate | 50 to 90 |
| Programmed Flow Rate | 90 to 100 |

The powerhead software may adjust the range of the purge/retract trigger 36 during retraction. The no-load retract speed may be a minimum of 6.0 ml/s. Thus, if the injector 20 is operating at this minimum of 6.0 ml/s, the injector 20 should adjust the range of the purge/retract trigger 36 so that a rate of 6.0 ml/s is achieved when the trigger 36 is fully engaged in the reverse direction. When the purge/retract trigger 36 is fully engaged in the reverse direction, therefore, the software may control the injector motor to deliver this minimum rate. The correlation of flow rate to the purge/retract trigger 36 position may be as shown in Table 2. The no-load retract speed may be a minimum of 6.0 ml/s. The position tolerance may be +/−2% of fully engaged.

TABLE 2

| Flow Rate (ml/s) | % of Fully Engaged |
| --- | --- |
| 0 | 0 to 12 (Dead Band) |
| 0.1 to 0.5 | 12 to 50 |
| 0.6 to 6.0 | 50 to 90 |
| 6.0 | 90 to 100 |

The powerhead software may display the volume position, by counting up as the ram 46 moves toward the home position. The powerhead software may additionally display the flow rate by calculating the average flow rate averaged over the previous 0.5 second. When the user releases the purge/retract trigger 36, the flow rate display may return to the programmed flow rate and the volume display may show the maximum programmable volume. The powerhead software may limit the reverse movement to a maximum flow rate of 1 ml/s for the first 1 ml. If the ram 46 is extended 20 ml or more and the operator engages the purge/retract trigger 36 at 90% to 100% in the reverse direction, the powerhead software may lock in the retract function so that the operator can release the flow rate trigger switch while the injector 20 continues to retract. If the ram 46 is not extended 20 ml or more, the powerhead software may not lock in the flow rate in the retract direction. When retracting the ram 46, if the flow rate is locked in and the user activates the purge/retract trigger 36, the powerhead software may deviate the lock-in feature and control the motor to the purge/retract trigger 36.

Pre-filled syringes, such as those commercially available from Mallinckrodt, may contain an extra 3 ml of contrast media or other fluid, over the labeled syringe size, to allow the user to purge air from the syringe and tubing and still have the fully labeled syringe volume available to inject. For example, a 125 ml syringe may contain 128 ml of contrast media. When the user inserts a new syringe 28 into the injector 20, the powerhead 22 may display the labeled syringe size selected and allow the user to purge up to 3 ml before the volume display decrements. If the user purges more than 3 ml, then the powerhead 22 may decrement the volume display 1 ml for every 1 ml of contrast expelled.

The powerhead software may enter the enabled state when the following sequence occurs: (1) the user opens and closes the syringe mount 26 when the ram 46 is in the home position; (2) the powerhead software verifies that all injection start signals are inactive, including start switches of the powerhead 22 and the external start signal; and (3) the user purges (i.e., expels) a minimum of 1 ml with the purge/retract trigger 36 and then releases the purge/retract trigger 36. When entering the enabled state, the powerhead software may illuminate the visual indicator 91 a first color, such as green. The injector 20 may remain in the enabled state if the user changes the injection parameters. The injector 20 may remain in the enabled state if the user retracts the ram 46 less than 5 ml. If the injector 20 is enabled and the user retracts the ram 46 greater than 5 ml, the powerhead software may disable the injection.

In one embodiment, when an injection is enabled and the user activates a start button on the powerhead control panel keypad 32 or when the injector 20 is enabled and a start command is received from the remote console 44, the powerhead 22 may start and run the programmed injection. While injecting, the powerhead software may display the programmed flow rate if the actual flow rate is within the flow rate performance tolerance. While injecting, the powerhead software may display the average flow rate if the actual flow rate is not within the flow rate performance tolerance. While injecting, the powerhead software may display the volume remaining for the programmed injection. While injecting, the powerhead software may sweep a tri-colored visual indicator 91 through the color spectrum to indicate that the injector 20 is running.

If the user activates the flow rate, volume, or start buttons on the powerhead control panel or remote console 44 while the injector 20 is running an injection, the powerhead software may pause the injection. If an injection is paused, the powerhead 22 may flash, at the fast rate, the programmed flow rate and the remaining programmed volume on the display activates an audible beep and flash the visual indicator 91, such as a tri-colored LED, in a second color, such as amber. For example, if 100 ml of a 125 ml syringe were programmed and the injector 20 was paused after 75 ml had been injected, then the injector 20 should display 25 ml for the volume remaining. If an injection is paused and the user activates the purge/retract trigger 36 in the "retract" direction, the powerhead 22 may disable auto injection mode, and transition to manual mode. If an injection is paused and the user activates the purge/retract trigger 36 in the "expel" direction, the powerhead 22 may display the actual flow rate and the remaining syringe volume without flashing and sweep the tri-color LED of the visual indicator 91 through the color spectrum while the ram 46 moves forward. When the user releases the purge/retract trigger 36, the powerhead software may display the programmed flow rate and the maximum programmable volume and flash the tri-color LED of the visual indicator 91 amber in color. If an injection is paused and the user activates the flow rate or volume buttons, the powerhead 22 may disable auto injection mode and transition to the manual mode. If the injection is paused and the user activates an injection start button on the powerhead 22 or remote console 44 before activating any of the other controls 90 or the purge/retract trigger 36, the powerhead software may resume the injection from where is was paused. If the user activates the purge/retract trigger 36 while in auto inject mode, the powerhead software may pause the injection.

When an injection is completed, the powerhead software may flash, at a slow rate, the average achieved flow rate and achieved volume values on the powerhead display. The cycle of the slow rate flash may be "on" for 1.5 seconds and "off" for 0.5 seconds. When an injection completes, the powerhead software may disable the injector 20 and turn off the tri-colored LED of the visual indicator.

After an injection completes and (1) the user activates the flow rate increment, flow rate decrement, volume increment, volume decrement, or start controls 90 on the powerhead control panel keypad 32 or remote console 44, (2) there is greater than 1 ml of volume remaining in the syringe 28, and (3) the user has not retracted the ram the powerhead software may: (1) display the programmed flow rate and maximum programmable volume, (2) re-enable the injection, and (3) activate the tri-color LED, of the visual indicator 91, the first color, such as green. If the user activates the purge/retract trigger 36 in the "expel" direction, the powerhead 22 may display the actual flow rate and the remaining syringe volume without flashing and sweep the tri-color LED, of the visual indicator 91, through the color spectrum while the ram 46 moves forward.

When the user releases the purge/retract trigger 36 the powerhead software may display the programmed flow rate and the maximum programmable volume and activate the tri-color LED, of the visual indicator 91, the first color. After an injection completes and there is 1 ml or less volume remaining in the syringe 28 the powerhead software may disable the injection.

An external start signal from the remote console 44 to the powerhead 22 is part of the console interface 89 between the powerhead 22 and remote console 44. The external start signal is used in conjunction with an injection start message from the remote console 44 to start an injection from the remote console 44. The powerhead software may start a programmed injection from the external start signal only if the following conditions are met: (1) the injection is enabled, (2) the external start signal activates, and (3) a message from the remote console 44 is received by the powerhead software within 500 milliseconds of the external start signal activation. If the powerhead software detects an external start signal activation and the injector 20 is not enabled, the powerhead software may ignore the external start signal, activate an audible beep and display a user error code for injection not enabled. If the powerhead software detects the external start signal and does not receive a start message, the powerhead software may disable auto inject mode and display the injector 20 failure code for injection start.

The powerhead 22 further includes a sensor for detecting when the user opens and closes the syringe mount 26.

If the user activates the purge/retract trigger 36 in the expel direction with the syringe mount 26 open the powerhead software may: (1) not allow the ram 46 to move in the expel direction, (2) display a user error code for the syringe clamp open, and (3) restore the original display when the user releases the purge/retract trigger 36 or closes the syringe mount 26.

If the powerhead software detects the syringe mount 26 opening during an injection, the software may stop injecting and flash, at a fast rate, an injector 20 fault code for syringe mount 26 open on the powerhead display 34 and disable the auto inject mode. If the user closes the syringe mount 26, the powerhead software may transition to manual mode and display the programmed flow rate and maximum programmable volume.

The powerhead software may correlate injector motor current to syringe pressure. In one embodiment, the powerhead software will not allow the syringe pressure to exceed 250 psi when the ram 46 is moving in the forward direction. If syringe pressure is approaching the pressure limit the powerhead software may reduce the flow rate of the injection to keep from exceeding the pressure limit. If the flow rate is reduced due to pressure limiting, the powerhead software may provide continual beeps from the audible annunciator and flash the flow rate on the display 34 at the fast rate while injecting. When a pressure limited injection completes, the powerhead software may stop the audible annunciator from beeping and flash the volume and flow rate at the slow rate. When retracting the ram 46, the powerhead software may limit the pressure. In one embodiment, the pressure during retraction of the ram 46 may be limited to a maximum of 100 psi.

The remote console 44 includes a timer for timing the elapsed time from the start of an injection to when the injector ram is retracted. The purpose of the timer is to assist the user in determining when to start an imaging scan after injecting contrast. The powerhead 22 may send messages to the remote console 44 containing injection elapsed time information for the remote console 44 to display on the injection timer. The powerhead 22 may not start the timer unless the injector 20 is first enabled.

It is expected that a user would typically use the auto inject feature to run an injection. In this scenario the user would first purge the injector 20 and stop. The injector 20 would be enabled at this point. The user would then start the injection using the start button on the powerhead 22 or the remote console 44. The timer would start timing when the start button is pressed. The powerhead 22 may reset and start the timer when an auto injection starts. During the injection the powerhead 22 may send messages to the remote console 44 with the injection elapsed time information to display on the timer.

In a different scenario, after purging and enabling the injector 20, a user could "manually" perform the injection by using the purge/retract trigger 36 instead of using the auto inject feature. In this scenario, the timer would start timing as soon as the ram 46 moved forward after being enabled. However, the timer should not display the time until a minimum of 10 ml volume was injected without stopping. If the user stopped injecting before 10 ml, the timer would reset to zero. When the user moves the injector ram 46 forward with the purge/retract trigger 36, the powerhead 22 may start the timer but send a message to the remote console 44 to display dashes until a minimum of 10 ml is expelled without stopping. If the user moves the ram 46 forward more than 10 ml, without stopping, the powerhead 22 may send the elapsed time to the remote console 44 to display on the timer. If the user stops expelling before 10 ml of contrast media or other fluid is expelled the powerhead 22 may stop the timer and send a message to the remote console 44 to continue to display dashes for the time.

In another scenario, the user may perform a "scout" injection prior to starting an auto injection. In this scenario the user would first purge and enable the injector 20, then manually inject a small amount of contrast, or other media, to verify proper needle placement. Several scout injections may be done before proper needle placement is verified. Once proper needle placement is verified the user then starts the injection using the start button on the powerhead 22 or the remote console 44. This scenario is covered in the above requirements for auto and manual injection. If the user performs a scout injection of less than 10 ml the timer display will remain with displayed dashes until the start button is pressed. If the user injects more than 10 ml, the timer will start and display time but reset to zero when the user starts the injection with the start button.

If an injection is paused, the powerhead 22 may allow the timer to continue to run and send messages to the remote console 44 with the injection elapse time. The powerhead 22 may stop the timer and send a message to the remote console 44 to display dashes when the ram 46 is retracted more than 5 ml.

The remote console 44 may include a momentary contact switch that the user may activate to turn 24 volt power "on" or "off" to the remote console 44 and the powerhead 22. When the remote console 44 detects the activation of this "soft" power switch 52, it sends a message to the powerhead 22 that 24 volt power is turning off. When the powerhead 22 receives a power down message from the remote console 44 the powerhead 22 may transition to the safe state.

The powerhead software contains a safe state to which the software transitions if an injector failure is detected. While in the safe state the injector 20 is prohibited from functioning in an unsafe manner. It is intended that, if possible, the ram 46 be retracted to the home position so the syringe 28 may be able to be removed from the injector 20. While in the safe state the powerhead software may not allow the injector ram 46 to move in the forward direction. The powerhead software may allow the user to retract the ram 46 to the home position at a maximum rate of 1 ml/s. While in the safe state the powerhead software may activate a periodic audible beep at the rate of on for one second and off for two seconds. While in the safe state the powerhead software may display the failure code of any detected injector malfunction. If more than one failure occurs the powerhead software may continually cycle through and display each failure code for at least 2 seconds. If the powerhead software enters the safe state it may stay in the safe state until power is cycled. Apart from the self-tests conducted at power-on, the powerhead software performs run time checks on hardware components to verify safe operation.

An LED is connected to the microcontroller I/O line for the software to toggle on/off so that a manufacturing technician has a visual indicator that the microcontroller is running. The powerhead software may toggle the "Alive" LED on and then off so that a manufacturing technician has a visual indicator that the microcontroller is running. If the microcontroller is reset, the powerhead software may display the microcontroller failure code and transition to the safe state.

The powerhead software may verify that the +24 volt power supply is between +20 volts and +28 volts within 500 milliseconds after starting an injection. If the +24 volt power supply is outside the tolerance range, the powerhead software may stop the motor and transition to the safe state. The powerhead software may verify that the +5 volt power supply is between +4.5 volts and +5.5 volts at a minimum every 30 seconds. If the +5 volt power supply is outside the tolerance range, the powerhead software may transition to the safe state.

The powerhead software may verify that the microcontroller is receiving motor encoder pulses whenever the software runs the motor. If the powerhead software does not detect any motor encoder pulses within 100 milliseconds of running the motor, the powerhead software may transition to the safe state.

The powerhead control panel keypad 32 may include two injection start switches that are activated by the user as one push-button for injection start. Two switches are used to as a redundant safety feature to avoid having a false start signal from a bad switch start an injection. If both start switches indicate an activation of the start button and the injector 20 is enabled, the powerhead software may activate the injector motor in the forward direction at the programmed values. If the injection completes and one of the start switches is active then the powerhead software may, until both start switches are inactive: (1) remain in the injection complete state, (2) display a start switch failure code, (3) allow the user to retract the ram 46 with the purge/retract trigger 36, and (4) not allow the user to move the ram 46 forward.

The powerhead motor assembly contains an encoder that provides position information back to the powerhead microcontroller. The encoder, however, does not provide absolute position information. Thus, when power is turned off and back on, the position information from the encoder is lost. Therefore, the powerhead 22 includes a ram home detector 50 that indicates when the ram 46 is at the fully retracted position or home position. When the ram 46 is being retracted, and the powerhead software determines from the encoder counts that the home position has been reached, and the sensor 140 of the home position detector 46 has not indicated a home position within +/−2 ml, the powerhead software may stop the motor and transition to the safe state. When the ram 46 is being retracted and the powerhead software determines the sensor 140 of the home position detector 50 indicates a home position while the encoder counts does not indicate a home position within +/−2 ml, the powerhead software may stop the motor and transition to the safe state.

The purge/retract trigger 36 includes sensors 116 that detect how much the user moves the trigger 36. If a zero point of the sensors drifts out of tolerance, the software could interpret the drift as a purge/retract trigger 36 activation. When the powerhead software detects purge/retract trigger 36 activation in the forward direction the software may check that all trigger sensors 116 indicate activation of the trigger 36 in the forward direction. When the powerhead software detects activation of the purge/retract trigger 36 in the reverse direction, the software may check that all trigger sensors 116 indicate activation of the trigger 36 in the reverse direction. If a purge/retract trigger sensor is out of tolerance, the powerhead software may transition to the safe state.

After an injection completes and the achieved average flow rate is not within the tolerance for a non-pressure limited injection, the powerhead software may alternate between displaying the achieved flow rate and the flow rate out of tolerance failure code until the user activates the purge/retract trigger 36 or any of the powerhead controls 90.

If the achieved volume is not within a specified tolerance, the powerhead software may alternate between displaying the achieved volume and the volume out of tolerance failure code until the user activates the purge/retract trigger 36 or any of the powerhead controls 90.

In one particular embodiment, if the powerhead software detects injector failure the software may display an indication code, such as "F", in the flow rate display and a number corresponding to the failure type in the volume display. In a particular embodiment, the failure codes are created and may be interpreted as follows. The hundred's digit represents the subsystem where the failure occurred. The number "0" in the hundred's digit represents the powerhead 22, a "1" represents remote console 44 (if connected), and a "3" represents the power pack 38. For example the failure code "F 004" is for the powerhead RAM memory failure while the failure code "F 104" is for the remote console 1 RAM memory failure. The failure codes in this particular embodiment of the software are as follows:

F X01 Microcontroller CPU Failure
F X02 Program Flash Memory CRC Failure
F X03 Data Flash Memory CRC Failure
F X04 RAM Memory Failure
F X05 Quad Timer Failure
F X06 A/D Converter Failure
F X07 PWM Failure
F X08 Interrupt Controller Failure
F X09 Clock PLL Failure
F X10 Microcontroller Watchdog Reset F X20 +24V Power Supply failure (+24V Power Supply out of tolerance)
F X21 +5V Power Supply failure (+5V Power Supply out of tolerance)
F 030 Encoder failure (no encoder counts when motor activated)
F 031 Encoder failure (encoder counts detected when motor not enabled)
F 032 Motor Relay failure (cut-out relay failure, relay stuck open or closed)
F 033 Motor failure (motor over current detected)
F 034 Motor failure (current detected when motor not enabled)
F X40 Start switch failure (one or both start switches are active)
F 050 Home sensor failure (no home position signal detected when ran encode indicates that the injector ram is at the home position)
F 051 Purge/Retract Trigger failure (zero position out of tolerance)
F 060 Achieved Flow Rate Out of Tolerance F 061 Achieved Volume Out of Tolerance
F 070 Powerhead—Remote Console Communication Failure
F 075 Remote Console—Power Pack Communication Failure
F 370 Dual Injector Interface failure If the user attempts to operate the injector 20 in an unsafe manner, the powerhead software may display an indicating signal, such as "ER", in the flow rate display and a number corresponding to the error type in the volume display. In one embodiment of the injector 20, these codes may be as follows:
ER 001 User attempts to start an injection from the powerhead when the injector is not enabled
ER 101 User attempts to start an injection from remote console when the injector is not enabled
ER 002 User attempts to move the ram forward with the syringe clamp open The manufacturing mode may allow personnel to perform diagnostics tests, calibrate sensors, and perform a burn-in cycle. The powerhead software may allow the manufacturing person to run diagnostic tests. The diagnostic tests at a minimum may run all the tests performed during power-on self-test. The powerhead manufacturing mode may allow calibration of the following sensors:
Purge/Retract Trigger Sensors
Pressure Limit
Ram Home Position Sensor
Syringe Clamp Sensor
The powerhead software may allow the calibration values to be sent out via interfaces 42, 89.

The manufacturing mode may allow the manufacturing person to select a "burn-in cycle" sub-mode where the powerhead software continuously runs an injection at a predetermined injection parameters.

The injector powerhead 22 may interface to the remote console 44 through a network and send messages to the remote console 44 with the following information:
Volume Display
Flow Rate Display
Timer Display
Audible Tone Frequency
Audible Tone Volume
Tri-Color LED Red Duty Cycle
Tri-Color LED Blue Duty Cycle
Tri-Color LED Green Duty Cycle The powerhead 22 may send messages to the remote console 44 as the event occurs or at a minimum of once per second. The powerhead 22 may receive messages from the remote console 44 with the following information:
Volume Increment/Decrement Button activation status and activation duration
Flow Rate Increment/Decrement Button activation status and activation duration
Injection Start Button activation
Soft Power Off Button activation
The injector powerhead 22 may also interface to a second system when a remote console 44 is connected.

As described above, the injector 20 of the present invention may include a remote console 44. The purpose of the remote console 44 is to provide the user a way to control and display the status of the powerhead 22 from a remote location, such as an imaging control room. The remote console 44 allows the user to program or change programmed parameters. When the powerhead 22 is enabled for an injection, the user can start the injector 20 or stop an injection in progress from the remote console 44.

The remote console 44 is based on a "master/slave" architectural design such that the remote console 44 functions as a "slave" to the powerhead 22 when the powerhead 22 is in the manual, auto inject, and syringe size selection modes. That is, the remote console 44 displays the flow rate and volume of the powerhead 22 and not what the user enters at the remote console 44. If the user changes the injection parameters from the remote console 44, the remote console 44 sends messages to the powerhead 22 reflecting the changes. The powerhead 22 implements the changes and sends messages back to the remote console 44 with the new information. This design reduces the possibility of the remote console 44 displaying something other than what the powerhead 22 is actually doing.

The remote console 44 includes software that functions as a "slave" to the powerhead 22. If the remote console 44 is powered on with no powerhead connection, the remote console 44 displays a powerhead-remote console communication fault code. The remote console 44 has a power-on self-test (POST) to check for proper remote console operation, and the safe state for serious injector malfunction. When power is applied, the remote console 44 performs an initialization of the microcontroller and system resources. After initialization, the remote console software runs a POST.

The POST then performs a CRC test of the program Flash memory and the data Flash memory. The POST then performs a memory test of all data and program RAM. The POST then performs a check of all microcontroller peripherals internal to the microcontroller used during the operation of the remote console 44. The remote console 44 POST checks for dual injector interface communication operation by sending a message to the dual injector interface to send status information over the remote console-power pack interface. If the remote console 44 does not receive a response from the dual injector interface, it fails the communication test. The POST checks the +24 power supply 40 for proper supply voltages of +24 VDC+/−4 volts and the +5 power supply 40 for +5 VDC+/−0.5 volts power supplies. The POST illuminates all visual indicators including all digits and segments in the 7-segment LED displays for a minimum of 3 seconds. The POST may activate the audible annunciator for a minimum of 500 milliseconds.

Upon successful completion of the POST, the remote console software may display the current software version on the LED display for a minimum of 3 seconds. If all self-tests pass, the remote console 44 may then check for the manufacturing mode. The remote console 44 will enter the manufacturing mode only if the user activates the volume increment and volume decrement at the same time within 3 seconds after POST completes. If the user activates any other button while the remote console software is checking for the manufacturing mode, the software skips the manufacturing mode check and proceeds to the operational mode. If any of the self-tests fail, the remote console 44 transitions to the safe state.

The remote console 44 may receive messages from the powerhead 22 with flow rate information and display the flow rate information on the remote console flow rate display. The remote console 44 may receive messages from the powerhead 22 with volume information and display the volume information on the remote console volume display. If the powerhead 22 sends a message to the remote console software to illuminate the injecting LED, the remote console 44 will illuminate the injecting LED on the remote console 44. If the powerhead 22 sends a message with an active error code, the remote console 44 may flash the error code at 500 milliseconds on and 200 milliseconds off. If the powerhead 22 sends a message with an active error code, the remote console 44 may activate the audible tone for one second on and one second off for three times. The remote console software may send any remote console control button activation to the powerhead 22. Controls 90 may include, but are not limited to, buttons for flow rate increment, flow rate decrement, volume increment, volume decrement, and injection start buttons.

The remote console 44 may include at least two injection switches that are activated by the user as one injection start push-button for starting an enabled injection. Two switches are used as a redundant safety feature to avoid having a false start signal from a bad switch to start an injection. The remote console 44 sends an injection start message to the powerhead 22 when the user activates the injection start button. When the user activates the injection start button, the remote console software verifies: (1) that both injection switches have been activated, and (2) that both injection switches have transitioned to the inactive state since the last activation. Following verification, the remote console software sends an injection start message to the powerhead 22.

When the user activates the volume increment button, the remote console software may send a message to the powerhead 22 indicating a volume increment button activation. When the user releases the volume increment button, the remote console software may send a message to the powerhead 22 indicating that the volume button is deactivated. The volume decrement button may operate in the same way as the volume increment button, except the remote console 44 sends messages to the powerhead 22 when the volume decrement button is activated or released.

When the user activates the flow rate increment button, the remote console software may send a message to the powerhead 22 indicating a flow rate increment button activation. When the user releases the flow rate increment button, the remote console software may send a message to the powerhead 22 indicating that the flow rate button is deactivated. The flow rate decrement button may operate in the same way as the flow rate increment button, except the remote console 44 sends messages to the powerhead 22 when the flow rate decrement button is activated or released.

The remote console software may display and flash an indicator, such as "PF", in the flow rate display when the powerhead 22 sends a message to display "PF". The "PF" indicator signals to the user that the injector 20 is in the pre-filled syringe selection mode. The remote console 44 may flash the "PF" at the rate sent from the powerhead 22.

An LED visual indicator may be connected to the microcontroller I/O line for the software to toggle on/off so that a manufacturing technician has a visual indicator that the microcontroller is running. The remote console software may toggle the "Alive" LED on and then off so that a manufacturing technician has a visual indicator that the microcontroller is running.

The remote console software may control the state of the tri-color LED visual indicator according to the message received from the powerhead 22. The states for the tri-color LED visual indicator may be: green, amber, red, blue, white, color sweep, and blank (no illumination).

Some imaging protocols require a delay of seconds, while others may require a delay of minutes, before starting the imaging scan. The remote console 44 includes a timer to assist the user in determining when to start an imaging scan after injecting contrast. The remote console 44 may include a timer for timing elapsed time from the start of an injection to when the injector ram is retracted. While the remote console 44 is on and the timer is not timing, the timer may display dashes in the minutes, tens of seconds, and seconds seven-segment LED display (i.e., "-:--"). The remote console 44 may display the elapsed time in a minutes and seconds format with a colon mark between the minutes and seconds. The remote console timer may range from 0 minutes, 0 seconds (0:00) to 19 minutes and 59 seconds (19:59). If the timer is less than 10 minutes, then the remote console 44 may blank the tens of minutes digit (for example, 9:59). If the timer is less than 1 minute, then the remote console 44 may display a zero in the minutes digit (for example, 0:09).

If the remote console 44 receives a message from the powerhead 22 to start the timer, the remote console 44 may reset the time to zero and start the time. The remote console 44 may continue to display dashes until the powerhead 22 sends a message to the remote console 44 to display the time The remote console 44 may stop the timer and display dashes when the remote console 44 receives a message from the powerhead 22 to stop the timer. If the timer reaches 19 minutes and 59 seconds (19:59) the timer may hold the time at 19 minutes and 59 seconds and flash the time display at the fast rate.

The remote console 44 further includes a momentary contact switch that the user may activate to turn 24 volt power on or off to the remote console 44 and the powerhead 22. The soft power switch 52 is not connected to power but to a microprocessor I/O line in the remote console 44. If the remote console 44 is powered up, the microprocessor can detect when the user toggles the soft power switch 52 to turn power off. The remote console 44 then sends a message over the remote console-power pack interface to turn 24 volt power off. If the remote console 44 is powered off, the microprocessor will be unable to detect user switch activation. However, a hardware circuit in the power pack 38 can detect switch activation through a hardware signal between the remote console 44 and the power pack 38. During this procedure, the power remains on in the power pack 38. The detection circuit then switches 24 volt power back on to the remote console 44 and powerhead 22.

When the remote console 44 is powered on and the user activates the soft power on/off switch 52, the remote console 44 may send a message over the remote console-power pack interface to disconnect 24 volt power to the powerhead 22 and remote console 44. The remote console 44 may delay a minimum of 20 milliseconds from when the user releases the soft power switch 52 until the power off message is sent over the remote console-power pack interface. When the remote console 44 is powered on and the user activates the soft power on/off switch 52, the remote console 44 may send a message to the powerhead 22 over the powerhead-remote console interface that 24 volt power is being disconnected. The soft power on/off feature may not be active before the remote console POST is completed. The soft power on/off feature may function while the injector 20 is in the safe mode. This assumes that the associated hardware for the soft power on/off is functional.

If the remote console 44 detects a communication failure with the powerhead 22, the remote console 44 may repeatedly attempt to communicate with the powerhead 22. If, after 5 seconds, the repeated attempts fail, the remote console 44 may display a communication failure and transition to the safe state.

The remote console 44 may display injector 20 failure codes sent from the powerhead 22. Further, the remote console 44 may display injector 20 user error codes sent from the powerhead 22.

The remote console software includes a safe state where the software transitions if a remote console failure is detected. While in the safe state, the remote console 44 is prohibited from functioning in an unsafe manner. Once in the safe state, the software may not exit from the safe state as long as power is applied to the remote console 44. While in the safe state, the software may not communicate with the powerhead 22. While in the safe state, the remote console software may send messages to the power pack 38 to disable all dual injector 20 relay outputs. While in the safe state, the remote console software may display the failure code of any detected remote console malfunction.

The injector 20 of the present invention has the ability to connect a second injector 20' together through the dual injector interface. This second injector 20' may be hand-held or may be wall, floor, or ceiling mounted. The interface 42 allows for the two injectors to work in tandem for delivering back to back injections. Typical use for two injectors includes a "saline push" where the first injector 20 delivers contrast followed by saline from the second injector 20'.

The dual injector interface is located in the power pack 38. Since the cable connecting the power pack 38 to the powerhead 22 does not include any spare signals to accommodate the dual injector interface directly, the remote console 44 serves as the link between the dual injector interface and the powerhead 22. Therefore, the remote console 44 includes a remote console-power pack interface. The remote console 44 polls the status of the dual injector interface via the remote console-power pack interface and sends messages to the powerhead 22 via the powerhead-remote console interface.

When the remote console 44 receives a message from the powerhead 22 to check for dual injector configuration, the remote console 44 may query the dual injector interface via the remote console-power pack interface. If another injector is connected to the dual injector interface, and the other injector is enabled, the remote console 44 may send the information to the powerhead 22 connected to the remote console 44.

The remote console 44 includes a microprocessor having internal non-volatile memory to store the software program and data constants. Manufacturing will need to update or change the contents of the non-volatile program and data memory. The manufacturing mode software may allow the manufacturing technician to reprogram the contents of the non-volatile program and data memory in the microprocessor.

Additional advantages and modifications will readily appear to those skilled in the art. The invention in its broader aspects is therefore not limited to the specific details, representative apparatus and methods, and illustrative examples shown and described. Accordingly, departures may be made from such details without departing from the scope or spirit of Applicant's general inventive concept.

What is claimed is:

1. A medical fluid injector comprising:
a drive ram having a longitudinal axis;
a motor to move the drive ram along the longitudinal axis;
a syringe mount comprising first and second members, the first member being mounted on a first pivot pin and pivotable about a first pivot axis, and the second member being mounted on a second pivot pin and pivotable about a second pivot axis different from the first pivot axis, wherein a line connecting the first and second pivot axes does not intersect the longitudinal axis of the drive ram, wherein the first and second members are pivotable between an open position for the syringe mount and a closed position for the syringe mount, wherein upper ends of the first and second members are closer to each other when the syringe mount is in the closed position compared to the open position, wherein the first and second members are biased to the closed position for the syringe mount by first and second biasing members, respectively, wherein the first and second members of the syringe mount, are engaged with a rearward end of a syringe to substantially immobilize the syringe relative to the motor when the syringe mount is in the closed position, wherein the first and second members of the syringe mount are disengaged from the rearward end of the syringe so that the syringe may be removed from the syringe mount when the syringe mount is in the open position, and wherein moving the syringe toward the longitudinal axis of the drive ram to install the syringe on the syringe mount engages the syringe with the first and second members to first move the syringe mount from the closed position to the open position, and thereafter the syringe mount is moved back to the closed position to retain the syringe within the syringe mount using the first and second biasing members;
a sensor for determining when the first and second members of the syringe mount are in the closed position and when the first and second members of the syringe mount are in the open position; and
an enable sequence comprising a plurality of different tasks that each must be completed before the motor can be operated to advance the drive ram for an injection, wherein one of the tasks of the enable sequence comprises the first and second members being moved to the open position and identified by the sensor and being moved to the closed position and identified by the sensor.

2. The medical fluid injector of claim 1, wherein each of the first and second members of the syringe mount comprises an arcuate surface.

3. The medical fluid injector of claim 1, wherein each of the first and second members of the syringe mount is biased toward the longitudinal axis of the drive ram by the first and second biasing members, respectively.

4. The medical fluid injector of claim 1, further comprising a housing that houses the motor and that allows the drive ram to extend out from the housing.

5. The medical fluid injector of claim 1, further comprising a console in electronic communication with the sensor and adapted to generate at least one console control signal for the medical fluid injector.

6. The medical fluid injector of claim 5, wherein the at least one console control signal is interrupted when the sensor determines that the first and second members of the syringe mount are in the open position.

7. The medical fluid injector of claim 5, wherein a first signal of the at least one console control signal signals the motor to move the drive ram along the longitudinal axis in a first direction, and wherein the first signal is prevented from being delivered to the motor when the sensor determines that the first and second members of the syringe mount are in the open position.

8. The medical fluid injector of claim 5, wherein the sensor is adapted to deliver a signal comprising positional information for the first and second members to the console.

9. The medical fluid injector of claim 1, further comprising software that is adapted to allow manual control of the medical fluid injector when the sensor determines that the first and second members are in the first closed position.

10. The medical fluid injector of claim 1, wherein the syringe has contrast media disposed therein.

11. The medical fluid injector of claim 1, further comprising a powerhead and a manually operable trigger, wherein the powerhead comprises the drive ram, the motor, and powerhead software, wherein the powerhead precludes movement of the drive ram in an expelling direction if the manually operable trigger is activated when the sensor detects the first and second members being in the open position for the syringe mount.

12. The medical fluid injector of claim 1, further comprising a powerhead that comprises the drive ram, the motor, and powerhead software, wherein the powerhead software terminates movement of the drive ram in an expelling direction and disables an auto inject mode of operation for the medical fluid injector if the sensor detects the first and second members being in the open position for the syringe mount.

13. A contrast media injector comprising:
an injector housing;
a drive ram bi-directionally movable along a longitudinal axis thereof;
a motor located within the injector housing and drivingly coupled to the drive ram;
a syringe cradle integral with the injector housing and designed to support a syringe at a fixed position relative to the motor; and
a syringe mount disposable in open and closed positions, and engageable with a rearward end of a body of a syringe so as to allow the drive ram to cause movement of a plunger of the syringe within and relative to the body of the syringe when the syringe mount is in the closed position, wherein:
the syringe mount includes first and second members;
the first member of the syringe mount is mounted on a first pivot pin and is pivotable relative to the syringe cradle about a first pivot axis, and the second member of the syringe mount is mounted on a second pivot pin and is pivotable relative to the syringe cradle about a second pivot axis different from the first pivot axis;
each of the first and second members of the syringe mount comprises an internal groove designed to accommodate an outwardly extending flange of the syringe;
the first and second members of the syringe mount are pivotable toward and away from each other such that the syringe mount may be disposed in the closed position and the open position, respectively, wherein upper ends of the first and second members are closer to each other when the syringe mount is in the closed position compared to the open position;
the first and second members are biased toward each other for the closed position of the syringe mount by first and second biasing members, respectively; and
moving the syringe toward the longitudinal axis of the drive ram to install the syringe on the syringe mount engages the syringe with the first and second members to first move the syringe mount from the closed position to the open position, and thereafter the syringe mount is moved back to the closed position to retain the syringe within the syringe mount using the first and second biasing members;
a sensor for determining when the syringe mount is in the open position and when the syringe mount is in the closed position; and
an enable sequence comprising a plurality of different tasks that each must be completed before the motor can be operated to advance the drive ram for an injection, wherein one of the tasks of the enable sequence comprises the syringe mount being moved to the open position and identified by the sensor, and being moved to the closed position and identified by the sensor.

14. The contrast media injector of claim 13, wherein each of the first and second members comprises metal.

15. The contrast media injector of claim 13, wherein each of the first and second members has an arcuate surface.

16. The contrast media injector of claim 13, wherein the first and second members are biased toward the longitudinal axis of the drive ram by the first and second biasing members, respectively.

17. The contrast media injector of claim 13, wherein the syringe cradle comprises a heating capability for warming contents of a syringe mounted to the contrast media injector.

18. The contrast media injector of claim 13, wherein the contrast media injector is a hand-held injector.

19. The contrast media injector of claim 13, further comprising a console in electronic communication with the sensor and adapted to generate at least one console control signal for the contrast media injector.

20. The contrast media injector of claim 19, wherein the at least one console control signal is interrupted when the sensor determines that the syringe mount is in the open position.

21. The contrast media injector of claim 19, wherein a first signal of the at least one console control signal signals the motor to move the drive ram along the longitudinal axis in a first direction, and wherein the first signal is prevented from being delivered to the motor when the sensor determines that the syringe mount is in the open position.

22. The contrast media injector of claim 19, wherein the sensor is adapted to deliver a signal comprising positional information for the first and second members of the syringe mount to the console.

23. The contrast media injector of claim 13, wherein software of the contrast media injector is adapted to allow manual control of the contrast media injector when the sensor determines that the syringe mount is in the closed position.

24. The contrast media injector of claim 13, further comprising a syringe engaged with the syringe mount.

25. The contrast media injector of claim 24, wherein the syringe comprises a body that includes an outwardly extending flange, and a plunger disposed within and movable relative to the body.

26. The contrast media injector of claim 25, wherein the flange is integral with a rear end of the body of the syringe.

27. The contrast media injector of claim 24, further comprising contrast media disposed within the syringe.

28. The contrast media injector of claim 13, wherein the first and second biasing members comprise first and second bias springs, respectively, journalled about the first and second pivot pins, respectively.

29. The contrast media injector of claim 13, wherein the first and second biasing members bias the first and second members, respectively, such that confronting faces of the first and second members are urged toward each other.

30. The contrast media injector of claim 24, wherein the syringe cradle extends to support the syringe along the majority of the length of the syringe.

\* \* \* \* \*

UNITED STATES PATENT AND TRADEMARK OFFICE
CERTIFICATE OF CORRECTION

PATENT NO. : 8,882,704 B2
APPLICATION NO. : 13/080499
DATED : November 11, 2014
INVENTOR(S) : Frank M. Fago et al.

Page 1 of 1

It is certified that error appears in the above-identified patent and that said Letters Patent is hereby corrected as shown below:

In The Claims

At Column 39, Claim 9, line 16, delete "first".
At Column 41, Claim 30, line 11, delete "the" and insert --a--.

Signed and Sealed this
Fourth Day of August, 2015

Michelle K. Lee
*Director of the United States Patent and Trademark Office*